United States Patent [19]

Osawa et al.

[11] Patent Number: 5,081,121

[45] Date of Patent: Jan. 14, 1992

[54] 4(1H)-QUINOLONE DERIVATIVES

[76] Inventors: Tatsushi Osawa; Hideo Ohta; Kohji Akimoto; Katsuhiko Harada; Hiroshi Soga; Yasuhiro Jinno, all of c/o Kirin Beer Kabushiki Kaisha Iyaku Kaihatsu Kenkyusho, 2-2, Souja-Mchi 1-Chome, Maebashi-Shi, Gunma-Ken, Japan

[21] Appl. No.: 356,370

[22] Filed: May 23, 1989

[30] Foreign Application Priority Data

May 24, 1988 [JP] Japan ................ 63-126249
Feb. 13, 1989 [JP] Japan ................ 1-33280
May 15, 1989 [JP] Japan ................ 1-120991

[51] Int. Cl.$^5$ ............. A61K 31/47; C07D 215/22
[52] U.S. Cl. .................. 514/312; 544/363; 546/153; 546/156
[58] Field of Search ............ 544/363; 546/156, 153; 514/312, 254

[56] References Cited

U.S. PATENT DOCUMENTS

| | | | |
|---|---|---|---|
| 2,558,211 | 6/1957 | Elderfield | 546/153 |
| 3,178,348 | 4/1965 | Bickerton | 514/312 |
| 4,168,311 | 9/1979 | Studeneer | 546/153 |
| 4,728,647 | 3/1988 | Benavides | 546/153 |

FOREIGN PATENT DOCUMENTS

| | | |
|---|---|---|
| 0206616A2 | 12/1980 | European Pat. Off. . |
| 014951A2 | 7/1985 | European Pat. Off. . |
| 0172004A2 | 2/1986 | European Pat. Off. . |
| 1188365 | 4/1970 | United Kingdom . |
| 2047691A | 12/1980 | United Kingdom . |
| 2085441A | 4/1982 | United Kingdom . |

OTHER PUBLICATIONS

Chem. Abstracts, vol. 41, No. 12, 6-20-47, Snyderetal, "Synthesis of 4-Hydroxyquinolines" col. 3801, Abstract 3801e.

Chem. Abstracts, vol. 88, No. 7, 2-13-78, Renavetatal. "Appln. of Phase Transfer" p. 254, col. 2, Abstract No. 50 616.

Jiegou Huaxue (J. Struct. Chem.), vol. 5, No. 1, 1 (1986).

Primary Examiner—C. Warren Ivy
Assistant Examiner—James H. Turnipseed
Attorney, Agent, or Firm—Ladas & Parry

[57] ABSTRACT

Quinolone derivatives having a quinolone structure:

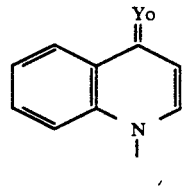

where Yo is O or S are disclosed, which are useful as cardiotonic agents. Typical examples of the quinolone derivatives include: 6,7-dimethoxy-4 (1H) quinolone (compound 6) and 5-hydroxy-6-methoxy-4(1H) quinolone (compound 1) as typical compounds of the formulae[I] and [I'], respectively, shown in the specification.

4 Claims, No Drawings

4(1H)-QUINOLONE DERIVATIVES

BACKGROUND OF THE INVENTION

1. Field of the Art

The present invention relates to 4(1H)-quinolone derivatives. These compounds generally act on cardiac muscle to increase its contractility, and some of these compounds increase selectively the cardiac muscle contractility without causing the extensive increase of heart rate. That is to say they have a cardiotonic effect.

2. Related Art

Cardiovascular diseases such as congestive heart failure, angina pectoris, nephredema or hepatic edema tend to increase with the advancement of age.

The factors for supporting the function of heart, are heart rate, preload, postload, cardiac muscle contracting force and the like. As the cause of congestive heart failure, all of the abnormalities of the aforementioned factors are significant, among which decrease of the cardiac muscle contractility is critical.

As a drug for increasing the contractility of the cardiac muscle, digitalis has traditionally been used. However, the range of the pharmaceutically active amount and the toxicity of digitalis is narrow, and digitalis tends to cause intoxication so that it is difficult to administer as a drug for enhancing the cardiac muscle contractility. Therefore, a strong cardiotonic agent having higher safety is desired as a substitute for digitalis.

In these years, as the remedies of heart failure, there have been developed salmazol derivatives, bipyridine derivatives, imidazolone derivatives and the like. However, most of these drugs are known to increase heart rate together with the increase of the contractility and thus to increase the oxygen consumption of the heart muscle, so that the failure of the heart muscle is often stimulated adversely.

DISCLOSURE OF THE INVENTION

Outline of the Invention

The object of the present invention is to provide a compound which has a heart muscle contractility enhancing effect and is suitable for improving the symptoms of the aforementioned cardiovascular failures and a cardiotonic agent containing it. The object is achieved by providing 4(1H)-quinolone derivatives represented by the following formulae [1] and [1'].

Thus, the quinolone derivatives and pharmaceutically acceptable salts thereof are characterized by having the structures represented by the following formulae [1] and [1']. The compounds represented by the formula [1'] are selected from the group consisting of the compounds specified following the formula [1'].

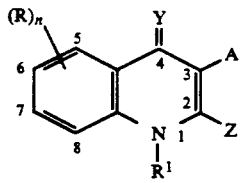
[1]

wherein respective substituents are defined as follows:
A is a hydrogen atom;
Y is an oxygen or sulfur atom;
R is a linear or branched alkoxy or alkenyloxy group having 1–4 carbon atoms, a benzyloxy group, a linear or branched alkyl or alkenyl group having 1–4 carbon atoms, a dialkylamino group having 1–4 carbon atoms, a phenyl group, chlorine atom, benzoyl group, an alkylsulfenyl, alkylsulfinyl or alkylsulfonyl group having 1–4 carbon atoms, or methylenedioxy group;

n denotes 2;

R's are placed at the positions 6 and 7 or 6 and 8 and may be the same or different;

$R^1$ is a hydrogen atom, a linear or branched alkyl or alkenyl group having 1–6 carbon atoms, a benzyl or substituted benzyl group having a substituent which is a $C_1$–$C_4$ lower alkoxy group and/or a halogen atom; and Z is a hydrogen atom, a cyclopropyl group, a 2- or 3-thienyl group, a 2- or 3-furyl group, a 2- or 3-pyrrolyl group or 2-, 3- or 4-pyridyl group.

A quinolone derivative selected from the group consisting of 5-hydroxy-6-methoxy-4(1H)-quinolone;
6-hydroxy-5-methoxy-4(1H)-quinolone;
8-hydroxy-7-methoxy-4(1H)-quinolone;
5-benzyloxy-6-methoxy-4(1H)-quinolone;
3-ethoxycarbonyl-5-methoxy-8-methoxymethoxy-4(1H)-quinolone;
8-cyano-4(1H)-quinolone;
5-cyano-4(1H)-quinolone;
6-acetoxy-4(1H)-quinolone;
6-acetoxy-1-acetyl-4(1H)-quinolone;
8-methoxy-1-methyl-4(1H)-quinolone;
5,8-diethoxy-4(1H)-quinolone;
8-i-propyl-4(1H)-quinolone;
8-methoxy-5-methyl-4(1H)-quinolone;
5-methoxy-8-phenyl-4(1H)-quinolone;
7,8-dimethoxy-4(1H)-quinolone;
5-methoxy-8-methylsulfenyl-4(1H)-quinolone;
6,7,8-trimethoxy-4(1H)-quinolone;
5-hydroxy-7-methoxy-4(1H)-quinolone;
8-cyano-3-ethoxycarbonyl-4(1H)-quinolone;
6,7-dimethoxy-3-methoxycarbonyl-1-methyl-4(1H)-quinolone;
3-ethoxycarbonyl-1-ethyl-6-methyl-4(1H)-quinolone;
7-ethoxy-3-ethoxycarbonyl-1-ethyl-6-methoxy-4(1H)-quinolone;
3-ethoxycarbonyl-8-methoxy-4(1H)-quinolone;
3-ethoxycarbonyl-8-methoxy-5-methyl-4(1H)-quinolone;
3-ethoxycarbonyl-8-methoxy-5-phenyl-4(1H)-quinolone;
7,8-dimethoxy-3-ethoxycarbonyl-1-ethyl-4(1H)-quinolone;
3-ethoxycarbonyl-1-ethyl-8-methoxy-6-methylsulfinyl-4(1H)-quinolone;
3-ethoxycarbonyl-1-ethyl-8-methoxy-6-methylsulfonyl-4(1H)-quinolone;
6,7-dimethoxy-3-hydroxymethyl-4(1H)-quinolone;
6,7-dimethoxy-3-hydroxymethyl-1-methyl-4(1H)-quinolone;
3-carboxyl-1-methyl-5,6,7-trimethoxy-4(1H)-quinolone;
8-acetyl-4(1H)-quinolone;
6-cyanomethyl-4(1H)-quinolone;
6-[2-trans-(2,5-dimethoxyphenyl)vinyl]-4(1H)-quinolone;
7,8-dimethyl-1-ethyl-4(1H)-quinolone;
7-[(1,3-dioxolan-2-yl)methoxy]-6-methoxy-4(1H)-quinolone;
6-methoxy-7-(2-methoxy)ethoxy-4(1H)-quinolone;

6-methoxy-7-methoxymethyl-4(1H)-quinolone;
1-ethyl-7-methyl-4(1H)-quinolone;
1-ethyl-6-methyl-4(1H)-quinolone;
1-ethyl-5-hydroxy-8-methyl-4(1H)-quinolone;
6-(2-hydroxy)ethyl-4(1H)-quinolone;
6-ethoxycarbonyl-4(1H)-quinolone;
1-ethyl-8-methoxy-5-phenyl-4(1H)-quinolone;
7-piperazinyl-4(1H)-quinolone;
8-(2-propenyl)-4(1H)-quinolone;
8-(2-trans-butenyl)-7-hydroxy-6-methoxy-4(1H)-quinolone;
1-ethyl-6-methoxy-4(1H)-quinolone;
6-ethoxy-1-ethyl-4(1H)-quinolone;
1,6-diethyl-4(1H)-quinolone;
6-ethoxyl-3-ethoxycarbonyl-8-methoxy-4(1H)-quinolone;
6-ethoxy-3-ethoxycarbonyl-1-ethyl-8-methoxy-4(1H)-quinolone;
8-ethoxy-3-ethoxycarbonyl-1-ethyl-6-methoxy-4(1H)-quinolone;
5-ethoxy-3-[(2-ethoxy)ethoxycarbonyl]-8-methoxy-4(1H)-quinolone;
3-ethoxycarbonyl-8-methoxy-4(1H)-thioquinolone;
7,8-dimethyl-3-ethoxycarbonyl-1-ethyl-4(1H)-quinolone;
5-acetoxy-3-ethoxycarbonyl-1-ethyl-8-methyl-4(1H)-quinolone;
3-ethoxycarbonyl-8-phenylsulfonyl-4(1H)-quinolone;
6-diethylamino-3-ethoxycarbonyl-8-methyl-4(1H)-quinolone;
1,6-diethyl-3-ethoxycarbonyl-4(1H)-quinolone;
3-carboxyl-6-ethoxy-1-ethyl-7-methoxy-4(1H)-quinolone;
3-carboxyl-1-ethyl-5-methyl-4(1H)-quinolone;
3-carboxyl-7,8-dimethyl-6-ethoxy-1ethyl-4(1H)-quinolone;
3-carboxyl-6-methoxy-1,7,8-trimethyl-4(1H)-quinolone;
3-carboxyl-1-ethyl-6-methyl-4(1H)-quinolone;
3-carboxyl-8-methoxy-5-phenyl-4(1H)-quinolone;
3-carboxyl-7-ethoxy-6-methoxy-1-methyl-4(1H)-quinolone;
3-carboxyl-7-ethoxy-6-methoxy-1-n-propyl-4(1H)-quinolone;
2-cyclopropyl-4(1H)-quinolone;
1-ethyl-2-(2-thienyl)-4(1H)-quinolone;
5-benzyloxy-6-methoxy-2-(3-pyridyl)-4(1H)-quinolone;
2-(2-thienyl)-4(1H)-quinolone;
6,7-dimethoxy-3-(4-phenylpiperidinyl)carbonyl-4(1H)-quinolone;
8-methoxy-5-methyl-3-(4-phenylpiperidinyl)carbonyl-4(1H)-quinolone;
8-methoxy-1-methyl-3-{1-[4-(3,4-methylenedioxybenzyl)piperazinyl]carbonyl}-4(1H)-quinolone;
1-ethyl-3-{1-[4-(2-methoxyphenyl)piperazinyl]carbonyl}-6-methyl-4(1H)-quinolone;
3-{1-[4-(2-methoxyphenyl)piperazinyl]carbonyl}-6-methyl-4(1H)-quinolone;
6,7-dimethoxy-1-ethyl-3-{1-[4-(4-nitrophenyl)piperazinyl]carbonyl}-4(1H)-quinolone;
6-[2-trans-(2,5-dimethoxyphenyl)vinyl]-1-ethyl-4(1H)-quinolone; and
2-cyclopropyl-1-ethyl-4(1H)-quinolone.

The present invention also relates to a cardiotonic agent. That is to say, the cardiotonic agent according to the present invention contains as the effective ingredients either one or two or more of the compounds represented by the general formulae [1] and [1'].

EFFECT OF THE INVENTION

The compounds according to the present invention exhibit an excellent effect of enhancing heart muscle contractility.

Some of these compounds possess an effect of selectively increasing heart muscle contractility without increase of heart rate.

DETAILED DESCRIPTION OF THE INVENTION

Compounds

As described above, the 4(1H)-quinolone derivatives according to the present invention are represented by the formulae [1] and [1'], and those represented by the formula [1'] is selected from the specific group of the compounds.

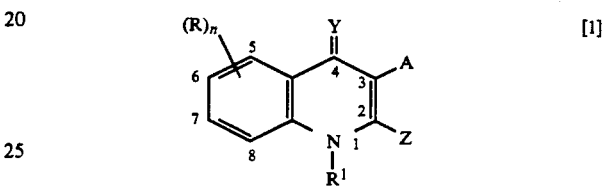

wherein respective substituents are defined as follows:
A is a hydrogen atom;
Y is an oxygen or sulfur atom;
R is a linear or branched alkoxy or alkenyloxy group having 1-4 carbon atoms, a benzyloxy group, a linear or branched alkyl or alkenyl group having 1-4 carbon atoms, a dialkylamino group having 1-4 carbon atoms, a phenyl group, a chlorine atom, a benzoyl group, an alkylsulfenyl, alkylsulfinyl or alkylsulfonyl group having 1-4 carbon atoms, or a methylenedioxy group;
n denotes 2;
Rs are placed at the position 6 and 7 or 6 and 8 and may be the same or different;
$R^1$ is a hydrogen atom, a linear or branched alkyl or alkenyl group having 1-6 carbon atoms, a benzyl or substituted benzyl group having a substituent which is a $C_1$-$C_4$ lower alkoxy group and/or a halogen atom; and
Z is a hydrogen atom, a cyclopropyl group, a 2- or 3-thienyl group, a 2- or 3-furyl group, a 2- or 3-pyrrolyl group or 2-, 3- or 4-pyridyl group.

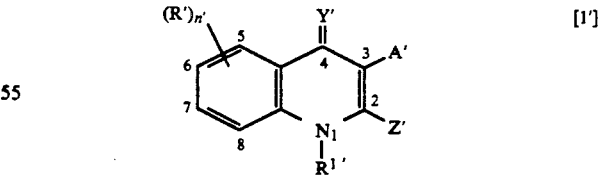

wherein the group of the compounds to be selected has been described above, and the respective substituents represent the corresponding substituents of the compounds to be selected.

The pharmaceutically acceptable salts of the compounds represented by the formulae [1] and [1'] are also involved in the present invention. The salts of such salts include, for example, inorganic salts such as a hydrochloride, a sulfate and the like, and organic salts such as a citrate, a maleate, a fumarate, a benzoate, a succinate, an acetate, a tartrate, and the like.

As the typical examples of the compound represented by the formula [1] according to the present invention, there are mentioned the compounds as follows:

6,7-dimethoxy-4(1H)-quinolone (Compound 6);
6-diethylamino-8-methyl-4(1H)-quinolone (Compound 9);
6,7-diethoxy-4(1H)-quinolone (Compound 10);
6,8-dimethoxy-4(1H)-quinolone (Compound 11);
6,7-dimethoxy-1-methyl-4(1H)-quinolone (Compound 13);
6,8-dimethoxy-1-ethyl-4(1H)-quinolone (Compound 16);
6,7-dimethoxy-1-(4-methoxybenzyl)-4(1H)-quinolone (Compound 17);
8-benzoyl-6-chloro-4(1H)-quinolone (Compound 18);
6-methoxy-8-methyl-4(1H)-quinolone (Compound 20);
6-benzyloxy-8-methoxy-4(1H)-quinolone (Compound 26);
1-ethyl-8-methoxy-6-methylsulfonyl-4(1H)-quinolone (Compound 29);
6-methoxy-8-methylsufenyl-4(1H)-quinolone (Compound 30);
8-ethoxy-6-methoxy-4(1H)-quinolone (Compound 47);
6-ethoxy-7-methoxy-4(1H)-quinolone (Compound 48);
6-ethoxy-1-ethyl-7-methoxy-4(1H)-quinolone (Compound 49);
7-i-propoxy-6-methoxy-4(1H)-quinolone (Compound 51);
7-n-butoxy-6-methoxy-4(1H)-quinolone (Compound 52);
7-allyloxy-6-methoxy-4(1H)-quinolone (Compound 53);
7-ethoxy-1-ethyl-6-methoxy-4(1H)-quinolone (Compound 58);
1-ethyl-6,7-methylenedioxy-4(1H)-quinolone (Compound 60);
7-ethoxy-6-methoxy-4(1H)-quinolone (Compound 62);
1-ethyl-6,7-methylenedioxy-4(1H)-quinolone (Compound 63);
1-n-butyl-7-ethoxy-6-methoxy-4(1H)-quinolone (Compound 68);
1-i-butyl-7-ethoxy-6-methoxy-4(1H)-quinolone (Compound 69);
6-chloro-8-methyl-4(1H)-quinolone (Compound 71);
6,7-dimethoxy-2-(2-furyl)-4(1H)-quinolone (Compound 94);
2-cyclopropyl-6,7-dimethoxy-4(1H)-quinolone (Compound 95);
2-cyclopropyl-7-ethoxy-6-methoxy-4(1H)-quinolone (Compound 98);
7-ethoxy-1-ethyl-2-(2-furyl)-6-methoxy-4(1H)-quinolone (Compound 101);
7-ethoxy-1-ethyl-6-methoxy-2-(2-thienyl)-4(1H)-quinolone (Compound 102);
1-allyl-2-cyclopropyl-7-ethoxy-6-methoxy-4(1H)-quinolone (Compound 103);
2-cyclopropyl-6,7-dimethoxy-1-(4-methoxybenzyl)-4(1H)-quinolone (Compound 104);
2-cyclopropyl-7-ethoxy-6-methoxy-1-(4-methoxybenzyl)-4(1H)-quinolone (Compound 112);
7-ethoxy-1-ethyl-6-methoxy-2-(3-pyridyl)-4(1H)-quinolone (Compound 114);
7-n-butoxy-2-cyclopropyl-6-methoxy-4(1H)-quinolone (Compound 115);
1-allyl-7-ethoxy-6-methoxy-2-(2-thienyl)-4(1H)-quinolone (Compound 116);
1-(2-trans-butenyl)-2-cyclopropyl-7-ethoxy-6-methoxy-4(1H)-quinolone (Compound 117);
7-n-butoxy-1-ethyl-2-(2-furyl)-6-methoxy-4(1H)-quinolone (Compound 118); and
2-cyclopropyl-6-ethoxy-7-methoxy-4(1H)-quinolone (Compound 119).

As the compounds represented by the formula [1'] according to the present invention, there are mentioned compounds as follows:

5-hydroxy-6-methoxy-4(1H)-quinolone (Compound 1);
6-hydroxy-5-methoxy-4(1H)-quinolone (Compound 2);
8-hydroxy-7-methoxy-4(1H)-quinolone (Compound 3);
5-benzyloxy-6-methoxy-4(1H)-quinolone (Compound 4);
3-ethoxycarbonyl-5-methoxy-8-methoxymethoxy-4(1H)-quinolone (Compound 5);
8-cyano-4(1H)-quinolone (Compound 7);
5-cyano-4(1H)-quinolone (Compound 8);
6-acetoxy-4(1H)-quinolone (Compound 12);
6-acetoxy-1-acetyl-4(1H)-quinolone (Compound 14);
8-methoxy-1-methyl-4(1H)-quinolone (Compound 15);
5,8-diethoxy-4(1H)-quinolone (Compound 19);
8-i-propyl-4(1H)-quinolone (Compound 21);
8-methoxy-5-methyl-4(1H)-quinolone (Compound 22);
5-methoxy-8-phenyl-4(1H)-quinolone (Compound 23);
7,8-dimethoxy-4(1H)-quinolone (Compound 24);
5-methoxy-8-methylsufenyl-4(1H)-quinolone (Compound 25);
6,7,8-trimethoxy-4(1H)-quinolone (Compound 27);
5-hydroxy-7-methoxy-4(1H)-quinolone (Compound 28);
8-cyano-3-ethoxycarbonyl-4(1H)-quinolone (Compound 31);
6,7-dimethoxy-3-methoxycarbonyl-1-methyl-4(1H)-quinolone (Compound 32);
3-ethoxycarbonyl-1-ethyl-6-methyl-4(1H)-quinolone (Compound 33);
7-ethoxy-3-ethoxycarbonyl-1-ethyl-6-methoxy-4(1H)-quinolone (Compound 34);
3-ethoxycarbonyl-8-methoxy-4(1H)-quinolone (Compound 35);
3-ethoxycarbonyl-8-methoxy-5-methyl-4(1H)-quinolone (Compound 36);
3-ethoxycarbonyl-8-methoxy-5-phenyl-4(1H)-quinolone (Compound 37);
7,8-dimethoxy-3-ethoxycarbonyl-1-ethyl-4(1H)-quinolone (Compound 38);
3-ethoxycarbonyl-1-ethyl-8-methoxy-6-methylsulfinyl-4(1H)-quinolone (Compound 39);
3-ethoxycarbonyl-1-ethyl-8-methoxy-6-methylsulfonyl-4(1H)-quinolone (Compound 40);
6,7-dimethoxy-3-hydroxymethyl-4(1H)-quinolone (Compound 41);
6,7-dimethoxy-3-hydroxymethyl-1-methyl-4(1H)-quinolone (Compound 42);
3-carboxyl-1-methyl-5,6,7-trimethoxy-4(1H)-quinolone (Compound 43);
8-acetyl-4(1H)-quinolone (Compound 44);
6-cyanomethyl-4(1H)-quinolone (Compound 45);
6-[2-trans-(2,5-dimethoxyphenyl)vinyl]-4(1H)-quinolone (Compound 46);
7,8-dimethyl-1-ethyl-4(1H)-quinolone (Compound 50);
7-[(1,3-dioxolan-2-yl)methoxy]-6-methoxy-4(1H)-quinolone (Compound 54);
6-methoxy-7-(2-methoxy)ethoxy-4(1H)-quinolone (Compound 55);

6-methoxy-7-methoxymethoxy-4(1H)-quinolone (Compound 56);
1-ethyl-7-methyl-4(1H)-quinolone (Compound 57);
1-ethyl-6-methyl-4(1H)-quinolone (Compound 59);
1-ethyl-5-hydroxy-8-methyl-4(1H)-quinolone (Compound 61);
6-(2-hydroxy)ethyl-4(1H)-quinolone (Compound 64);
6-ethoxycarbonyl-4(1H)-quinolone (Compound 65);
1-ethyl-8-methoxy-5-phenyl-4(1H)-quinolone (Compound 66);
7-piperazinyl-4(1H)-quinolone (Compound 67);
8-(2-propenyl)-4(1H)-quinolone (Compound 70);
8-(2-trans-butenyl)-7-hydroxy-6-methoxy-4(1H)-quinolone (Compound 72);
1-ethyl-6-methoxy-4(1H)-quinolone (Compound 73);
6-ethoxy-1-ethyl-4(1H)-quinolone (Compound 74);
1,6-diethyl-4(1H)-quinolone (Compound 75);
6-ethoxy-3-ethoxycarbonyl-8-methoxy-4(1H)-quinolone (Compound 76);
6-ethoxy-3-ethoxycarbonyl-1-ethyl-8-methoxy-4(1H)-quinolone (Compound 77);
8-ethoxy-3-ethoxycarbonyl-1-ethyl-6-methoxy-4(1H)-quinolone (Compound 78);
5-ethoxy-3-[(2-ethoxy)ethoxycarbonyl]-8-methoxy-4(1H)-quinolone (Compound 79);
3-ethoxycarbonyl-8-methoxy-4(1H)-thioquinolone (Compound 80);
7,8-dimethyl-3-ethoxycarbonyl-1-ethyl-4(1H)-quinolone (Compound 81);
5-acetoxy-3-ethoxycarbonyl-1-ethyl-8-methyl-4(1H)-quinolone (Compound 82);
3-ethoxycarbonyl-8-phenylsulfonyl-4(1H)-quinolone (Compound 83);
6-diethylamino-3-ethoxycarbonyl-8-methyl-4(1H)-quinolone (Compound 84);
1,6-diethyl-3-ethoxycarbonyl-4(1H)-quinolone (Compound 85);
3-carboxyl-6-ethoxy-1-ethyl-7-methoxy-4(1H)-quinolone (Compound 86);
3-carboxyl-1-ethyl-5-methyl-4(1H)-quinolone (Compound 87);
3-carboxyl-7,8-dimethyl-6-ethoxy-1-ethyl-4(1H)-quinolone (Compound 88);
3-carboxyl-6-methoxy-1,7,8-trimethyl-4(1H)-quinolone (Compound 89);
3-carboxyl-1-ethyl-6-methyl-4(1H)-quinolone (Compound 90);
3-carboxyl-8-methoxy-5-phenyl-4(1H)-quinolone (Compound 91);
3-carboxyl-7-ethoxy-6-methoxy-1-methyl-4(1H)-quinolone (Compound 92);
3-carboxyl-7-ethoxy-6-methoxy-1-n-propyl-4(1H)-quinolone (Compound 93);
2-cyclopropyl-4(1H)-quinolone (Compound 96);
1-ethyl-2-(2-thienyl)-4(1H)-quinolone (Compound 97);
5-benzyloxy-6-methoxy-2-(3-pyridyl)-4(1H)-quinolone (Compound 99)
2-(2-thienyl)-4(1H)-quinolone (Compound 100);
6,7-dimethoxy-3-(4-phenylpiperidinyl)carbonyl-4(1H)-quinolone (Compound 105)
8-methoxy-5-methyl-3-(4-phenylpiperidinyl)carbonyl-4(1H)-quinolone (Compound 106);
8-methoxy-1-methyl-3-{1-[4-(3,4-methylenedioxybenzyl)-piperazinyl]carbonyl}-4(1H)-quinolone (Compound 107);
1-ethyl-3-{1-[4-(2-methoxyphenyl)piperazinyl]carbonyl}-6-methyl-4(1H)-quinolone (Compound 108);
3-{1-[4-(2-methoxyphenyl)piperazinyl]carbonyl}-6-methyl-4(1H)-quinolone (Compound 109);
6,7-dimethoxy-1-ethyl-3-{1-[4-(4-nitrophenyl)-piperazinyl]carbonyl}-4(1H)-quinolone (Compound 110);
6-[2-trans-(2,5-dimethoxyphenyl)vinyl]-1-ethyl-4(1H)-quinolone (Compound 111);
2-cyclopropyl-1-ethyl-4(1H)-quinolone (Compound 113).

Among the above-described compounds represented by the formula [1'] are more preferred the following compounds:

3-ethoxycarbonyl-8-methoxy-5-phenyl-4(1H)-quinolone (Compound 37);
7-piperazinyl-4(1H)-quinolone (Compound 67);
8-(2-trans-butenyl)-7-hydroxy-6-methoxy-4(1H)-quinolone (Compound 72);
6-ethoxy-3-ethoxycarbonyl-8-methoxy-4(1H)-quinolone (Compound 76);
6-ethoxy-3-ethoxycarbonyl-1-ethyl-8-methoxy-4(1H)-quinolone (Compound 77);
8-ethoxy-3-ethoxycarbonyl-1-ethyl-6-methoxy-4(1H)-quinolone (Compound 78);
6-diethylamino-3-ethoxycarbonyl-8-methyl-4(1H)-quinolone (Compound 84);
1,6-diethyl-3-ethoxycarbonyl-4(1H)-quinolone (Compound 85);
3-carboxyl-7-ethoxy-6-methoxy-1-methyl-4(1H)-quinolone (Compound 92);
1-ethyl-2-(2-thienyl)-4(1H)-quinolone (Compound 97);
2-(2-thienyl)-4(1H)-quinolone (Compound 100); and
2-cyclopropyl-1-ethyl-4(1H)-quinolone (Compound 113).

Some of the above-described compounds represented by the formulae [1] and [1'] have substantially no heart rate enhancing effect when they show the effect of increasing heart muscle contractility.

PRODUCTION OF THE COMPOUNDS

The compounds represented by the formulae [1] and [1'] can be prepared by a variety of routes such as reactions of the routes (A)-(F) illustrated below:

In the reactions specified below, Me, Et, $^iPr$, $^tBu$, Ac, Ph and Ts represent a methyl group, an ethyl group, an i-propyl group, a t-butyl group, an acetyl group, a phenyl group and a paratoluenesulfonyl group, respectively. Also, in the reaction equations in the routes (A)-(E), R, R' and n may be replaced with R', $R^{1'}$ and n', respectively, and R or R', $R^1$ or $R^{1'}$, and n or n' have the same meanings as defined in the general formulae [1] and [1'].

Route (A): This method is illustrated as follows:

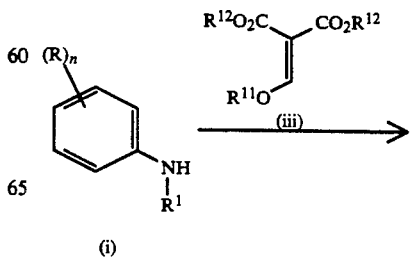

-continued

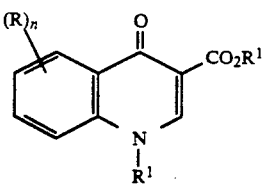

(ii)

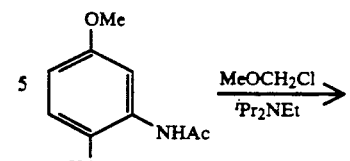

The aniline derivative (i) is condensed with an alkoxymethylenemalonic acid ester (iii) be heating at a temperature of 100°–120° C., and the condensate is heated in a high-boiling solvent such as diphenyl ether and the like at 250°–270° C. for 0.5–3 hours, preferably 1.5 hours to obtain a cyclized product (ii). In the formula (iii), the lower alkoxy group ($OR^{11}$) having 1–4 carbon atoms is typically an ethoxy group, and $R^{12}$ represents a lower alkyl group having 1–4 carbon atoms, typically an ethyl group. The groups $R^{12}$ may be the same or different. The product is isolated and purified in an ordinary way.

A typical reaction is illustrated in the following.

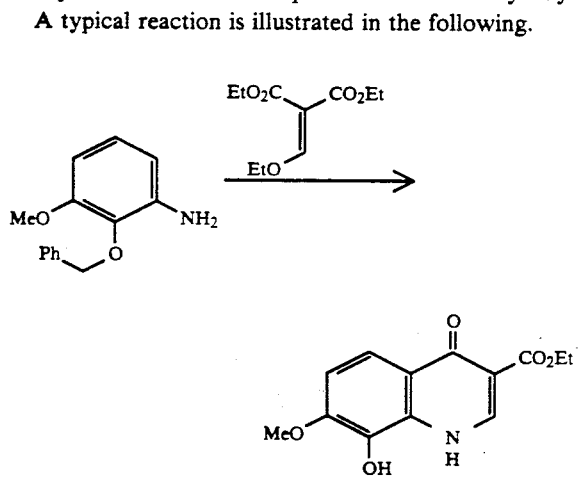

and

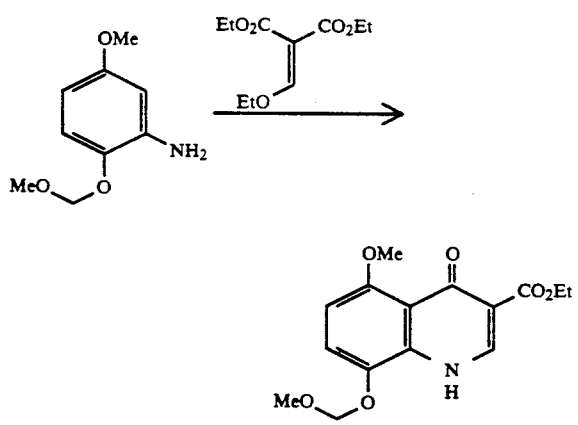

The starting material represented by the formula (i) can be prepared in an ordinary manner. The routes to these materials, most of which will be described in the preparation examples hereinafter, are typically illustrated as follows:

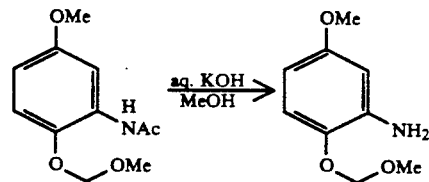

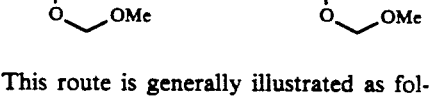

Route (B) This route is generally illustrated as follows:

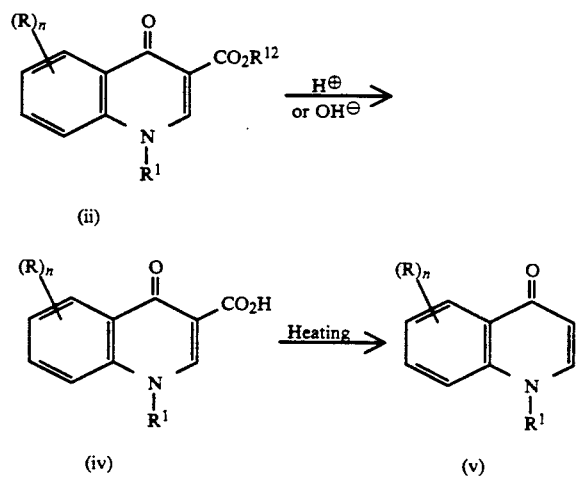

In order to obtain the compound represented by the formula [1] wherein A is H, the ester group is first hydrolyzed into a $CO_2H$ group, which is decarboxylated in a subsequent step. In other words, the compound represented by the formula (ii) is hydrolyzed with an appropriate base such as potassium hydroxide, sodium hydroxide or lithium hydroxide or an appropriate acid such as hydrochloric acid or sulfuric acid in methanol-water (in a ratio from 95:5 to 50:50, preferably 60:40) to obtain a carboxylic acid (iv). This carboxylic acid is heated under reflux in a high-boiling solvent such as diphenyl ether or the like for 0.5–6 hours to prepare a quinolone compound (v). The reaction is preferably performed under the stream of an inert gas such as argon or the like. The product is isolated and purified in an ordinary manner. The reaction is typically illustrated as follows:

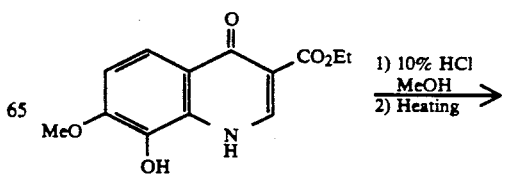

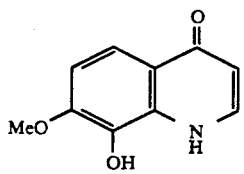

Route (C) This route is generally illustrated as follows:

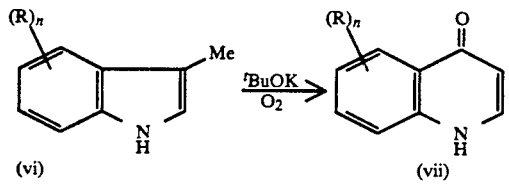

This reaction is conducted in an appropriate aprotic solvent, preferably in dimethylformamide (DMF) under the stream of oxygen in the presence of a strong base such as sodium hydride, potassium hydride, lithium hydride, sodium amide, preferably potassium t-butoxide at a room temperature to obtain a quinolone compound. The product is isolated and purified in an ordinary manner.

The reactions are typically illustrated as follows:

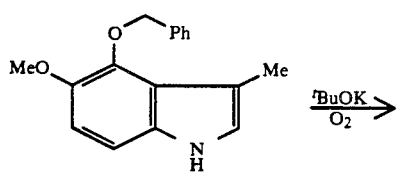

and

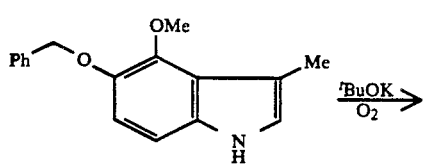

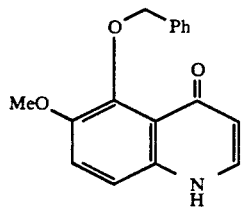

The starting material represented by the formula (vi) can be prepared in an ordinary manner. The routes to these materials, most of which will be described in the preparation examples hereinafter, are typically illustrated as follows:

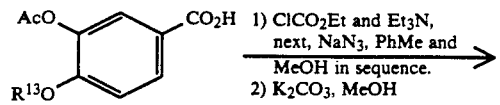

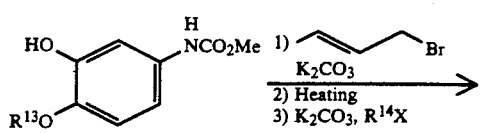

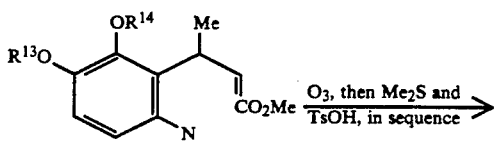

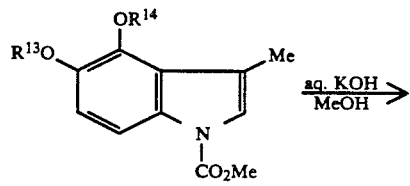

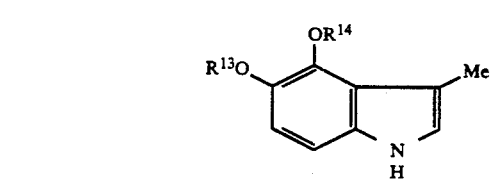

wherein $R^{13}$ and $R^{14}$ represent Me or $CH_2Ph$, respectively, and X represents a halogen atom.

Route (D) This route is generally illustrated as follows:

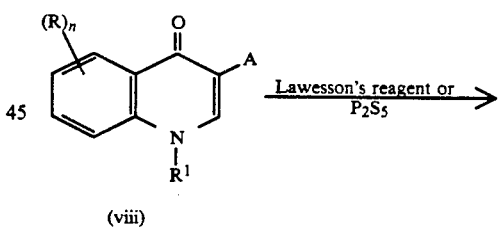

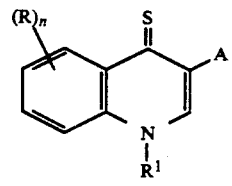

The compound wherein Y is S can be obtained by heating the compound (viii) with a Lawesson's reagent or $P_2S_5$ in an aromatic solvent such as benzene, xylene, o-dichlorobenzene, preferably toluene, or tetrahydrofuran. The product is isolated and purified in an ordinary manner.

Route (E) This route is generally illustrated as follows:

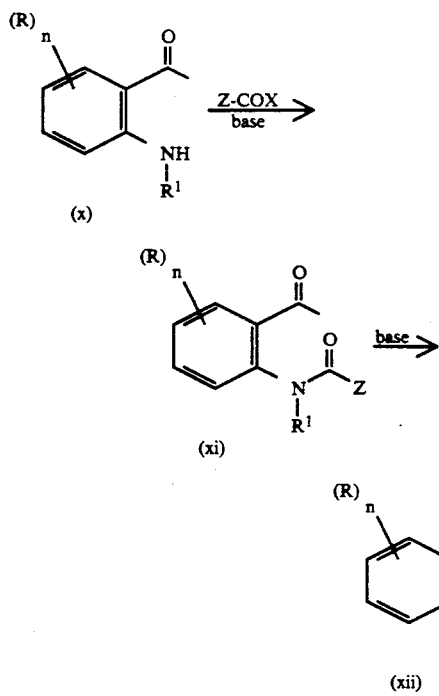

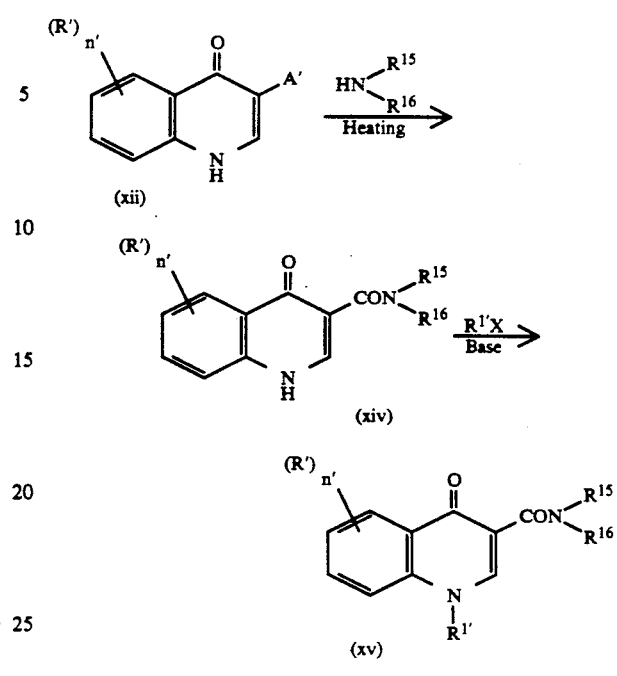

wherein X represents a halogen atom.

This route comprises two reactions, the first of which is acylation of the amino group. In this reaction, the amine (x) is reacted with an acid halide in a solvent such as tetrahydrofuran, dimethylformamide, methylene chloride, chloroform or the like in the presence of a base such as triethylamine, dimethylaminopyridine, sodium hydride, potassium hydride, calcium carbonate or the like to form the compound (xi). This compound is then reacted with a base such as sodium hydride, 'BuOK (potassium t-butoxide) or the like in a solvent such as tetrahydrofuran, dimethylformamide, t-butanol or the like at a room temperature or under a heating condition to obtain the compound (xii).

These reactions are typically illustrated as follows:

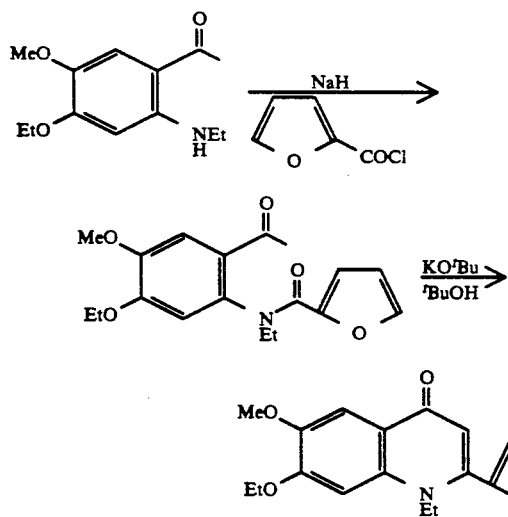

Route (F) This route is intended to obtain the compound (xv) below which is represented by the general formula [1'] and is generally illustrated as follows:

wherein
n' denotes 0–4;
A' represents a lower alkoxycarbonyl group having 1–4 carbon atoms or carboxyl group;
$R^{15}$ and $R^{16}$ represent independently a hydrogen atom or an alkyl group having 1–4 carbon atoms, or may form a heterocyclic ring containg a nitrogen atom, an oxygen atom and/or a sulfur atom; and
$R^{1'}$ has the same meaning as defined in the compounds represented by the formula [1'].

The compound (xiv) is obtained by heating the compound represented by the formula (xiii) together with an amine such as a piperidine or piperazine derivative or the like in a solvent such as pyridine or the like. This compound is then reacted with a variety of halides in a polar solvent such as dimethylformamide or the like in the presence of a base such as potassium carbonate or the like to obtain the compound (xv).

The reactions are typically illustrated as follows:

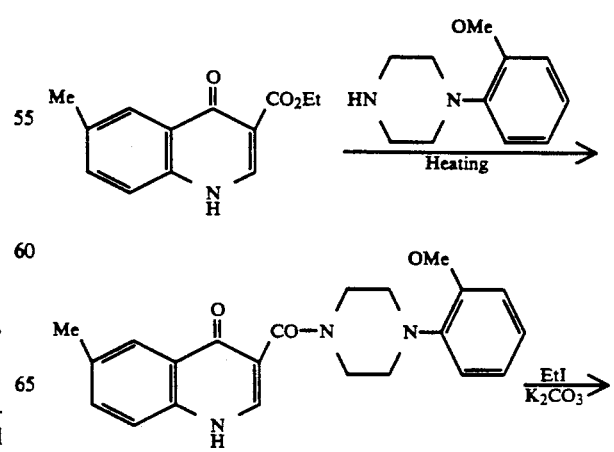

-continued

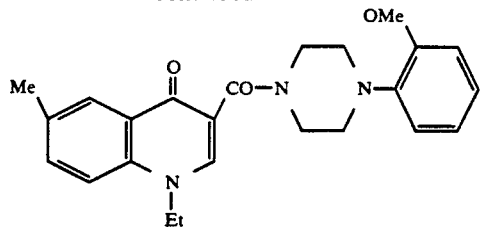

USEFULNESS OF THE COMPOUNDS ACCORDING TO THE PRESENT INVENTION: CARDIOTOMIC AGENTS

The quinolone compounds represented by the formulae [1] and [1'] according to the present invention and salts thereof have an effect of enhancing heart muscle contractility and thus are useful as cardiotonic agents. Typical quinolone compounds according to the present invention include the aforementioned compounds (1)–(119). Some of these compounds, as described hereinbefore, have an effect of increasing selectively heart muscle contracting force without substantially increasing heart rate and may be used effectively as cardiotonic agents.

The dose of the compound according to the present invention to be administered as cardiotonic agents is not critical, and the compound can be usually administered orally or parenterally, for example in the form of intravenous injection or cataplasm as an endermic, once a day in a dose from 100 to 1,000 mg/day for an adult patient (having an average body weight of 60 kg).

The forms of the preparation to be administered include for example, powder, grains, granules, tablets, capsules, injections and the like. On making a preparation of the compound, it can be produced with a conventional carrier for preparations in an ordinary manner.

The present invention will be described in detail with reference to Examples below without being limited thereto unless they will departs from the spirit and scope of the invention.

EXPERIMENTAL EXAMPLES

Synthesis of the Compounds

Synthesis and physico-chemical properties of the compounds according to the present invention are illustrated below. The measurements of NMR are expressed as ppm with use of tetramethylsilane as an internal standard. Temperatures are expressed in centigrade. No correction of melting points is made. Parts indicate parts by volume.

EXPERIMENTAL EXAMPLE 1

Two grams of 2-benzyloxy-3-methoxyaniline and 2.3 g of diethyl ethoxymethylenemalonate were heated at a temperature of 100°–120° C. for 1 hour. Fifty milliliter of diphenyl ether was added to the mixture, and the resulting mixture was further heated at 250°–270° C. for 1.5 hours. After the mixture was cooled down to room temperature, it was purified by silica gel column chromatography (Wako Gel C-200, 100 g). Elution with a mixed solvent of chloroform (95 parts) and methanol (5 parts) gave 980 mg of 3-ethoxycarbonyl-8-hydroxy-7-methoxy-4(1H)-quinolone.

M.p. 233°–236° (recrystallized from chloroform-n-hexane).

IR $\nu_{max}$KBr (cm$^{-1}$): 3430, 1720, 1635.

$^1$H-NMR (CDCl$_3$—CD$_3$OD (4:1), 100 MHz) δ:1.38 (3H, t, J=7.0 Hz), 3.96 (3H, s), 4.36 (2H, q, J=7.0 Hz), 7.04 (1H, d, J=8.8 Hz), 7.86 (1H, d, J=8.8 Hz), 8.54 (1H, s).

FD-MS (m/z): 263 (M+).

EXPERIMENTAL EXAMPLE 2

3-Ethoxycarbonyl-8-hydroxy-7-methoxy-4(1H)-quinolone (950 mg) was heated together with 2N HCl (30 ml) for 1 hour, and the resulting precipitate was collected by filtration, washed with water and dried to obtain a carboxylic acid (800 mg). This carboxylic acid (160 mg) was suspended in diphenyl ether (15 ml) and heated at 250°–270° C. under a stream of argon for 1 hour. After the mixture was left to cool down to room temperature, it was purified by silica gel column chromatography (Wako Gel C-200, 10 g). Elution with a mixed solvent of chloroform (90 parts) and methanol (10 parts) gave 130 mg of 8-hydroxy-7-methoxy-4(1H)-quinolone (Compound 3).

M.p. 228°–230° (recrystallized from chloroform-methanol-n-hexane).

IR $\nu_{max}$KBr (cm$^{-1}$): 1640, 1620.

$^1$H-NMR (DMSO-d$_6$, 500 MHz) δ:3.91 (3H, s), 5.89 (1H, d, J=7.4 Hz), 7.07 (1H, d, J=8.5 Hz), 7.55 (1H, d, J=8.5 Hz), 7.66 (1H, d, J=7.4 Hz), 9.68 (1H, s) 11.14 (1H, s).

$^{13}$C-NMR (DMSO-d$_6$, 125 MHz) δ:56.2, 107.3, 109.3, 115.5, 120.6, 131.1, 133.6, 139.1, 147.7, 176.3.

FD-MS (m/z): 191 (M+).

EXPERIMENTAL EXAMPLE 3

5-Methoxy-2-methoxymethoxyaniline (3.6 g) and diethyl ethoxymethylenemalonate (4.5 g) were heated at a temperature of 100°–120° C. for 1 hour. Eighty milliliter of diphenyl ether was added to the mixture, and the resulting mixture was further heated at 250°–260° C. for 1.5 hours. After the mixture was left to cool down to room temperature, it was purified by silica gel column chromatography (Wako Gel C-200, 140 g). Elution with a mixed solvent of chloroform (97 parts) and methanol (3 parts) gave 3.0 g of 3-ethoxycarbonyl-5-methoxy-8-methoxymethoxy-4(1H)-quinolone (compound 5).

M.p. 175°–177° (recrystallized from chloroform-n-hexane);

IR $\nu_{max}$CHCl$_3$ (cm$^{-1}$): 3420, 1725, 1670.

$^1$H-NMR (CDCl$_3$, 100 MHz) δ:1.37 (3H, t, J=7.0 Hz), 3.46 (3H, s), 3.90 (3H, s), 4.37 (2H, q, J=7.0 Hz), 5.23 (2H, s), 6.70 (1H, d, J=8.5 Hz), 7.33 (1H, d, J=8.5 Hz), 8.76 (1H, s).

FD-MS (m/z): 307 (M+).

5-Methoxy-2-methoxymethoxyaniline as the starting material was a novel compound and was prepared in the following manner.

2-Hydroxy-5-methoxyacetanilide (700 mg) was dissolved in methylene chloride (30 ml), and ethyldiisopropylamine (550 mg) and an 80% chloromethyl methyl ether (460 mg) were added to the solution. The mixture was stirred at room temperature for 15 hours, washed with 5% hydrochloric acid and saturated saline and dried over sodium sulfate, and the solvent was distilled off under reduced pressure. The residue was purified by silica gel column chromatography (Wako Gel C-200, 20 g). Elution with a mixed solvent of n-hexane (60 parts) and ethyl acetate (40 parts) gave 5-methoxy-2-methoxymethoxyacetanilide (810 mg).

IR $\nu_{max}$CHCl$_3$ (cm$^{-1}$): 3440, 1690.

$^1$H-NMR (CDCl$_3$, 100 MHz) δ:2.19 (3H, s), 3.49 (3H, s), 3.78 (3H, s), 5.13 (2H, s), 6.53 (1H, dd, J=2.9 Hz, 9.1 Hz), 7.02 (1H, d, J=9.1 Hz), 7.78 (1H, br s), 8.05 (1H, d, J=2.9 Hz).

FD-MS (m/z): 225 (M+).

5-Methoxy-2-methoxymethoxyacetanilide (810 mg) was dissolved in methanol (15 ml). A solution of potassium hydroxide (5.0 g) in water (9 ml) was added to the solution prepared above, and the mixture was heated under reflux for 2 hours. The reaction mixture was poured into water and extracted with chloroform. The extract was washed with saturated saline and dried over sodium sulfate, and the solvent was distilled off under reduced pressure to obtain 5-methoxy-2-methoxymethoxy aniline (680 mg).

IR $\nu_{max}$CHCl$_3$ (cm$^{-1}$): 3460, 3370, 1620.

$^1$H-NMR (CDCl$_3$, 100 MHz) δ:3.49 (3H, s), 3.72 (3H, s), 3.77 (2H, br s), 5.09 (3H, s), 6.15∼6.31 (2H, m), 6.91 (1H, d, J=8.5 Hz).

EXPERIMENTAL EXAMPLE 4

4-Benzyloxy-5-methoxy-3-methylindole (3.5 g) was dissolved in dimethylformamide (40 ml), and potassium t-butoxide (3.3 g) was added to the mixture. The resulting mixture was stirred at room temperature under a stream of oxygen for 5 days, poured into water and extraction with ethyl acetate was conducted. The extract was washed with saturated saline and dried over sodium sulfate, and the solvent was distilled off under reduced pressure. The residue was purified by silica gel column chromatography (Wako Gel C-200, 80 g). Elution with a mixed solvent of chloroform (92 parts) and methanol (8 parts) gave 5-benzyloxy-6-methoxy-4(1H)-quinolone (compound 4; 390 mg).

M.p. 171°-172° (recrystallized from chloroform-methanol-n-hexane).

IR $\nu_{max}$KBr (cm$^{-1}$): 3420, 1610.

$^1$H-NMR (CDCl$_3$: CD$_3$OD (4:1), 100 MHz) δ:3.88 (3H, s), 5.13 (2H, s), 6.24 (1H, d, J=7.1 Hz), 7.25∼7.63 (7H, m), 7.68 (1H, d, J=7.1 Hz).

FD-MS (m/z): 281 (M+).

4-Benzyloxy-5-methoxy-3-methylindole as the starting material was a novel compound and was prepared in the following manner.

3-Acetoxy-4-methoxybenzoic acid (5.0 g) was dissolved in the mixture of acetone (95 ml) and water (5 ml). To this solution were added ethyl chlorocarbonate (3.4 g) and triethylamine (2.9 g) under ice-cooling, and the mixture stirred for 0.5 hour. To this mixture was further added a solution of sodium azide (2.3 g) in water (10 ml), and the resulting mixture was further stirred at 0° for 1 hour, poured into ice-water, and extracted with ether. The extract was washed with saturated saline and dried over sodium sulfate, and the solvent was distilled off under reduced pressure to obtain a crude acyl azide. The product, without purification, was dissolved in toluene (50 ml), and the solution was heated under reflux for 1 hour. The solvent was distilled off under reduced pressure. The crude isocyanate was dissolved in methanol (100 ml), and the mixture was heated under reflux for 1 hour. After the mixture was left to cool to room temperature, potassium carbonate (5.0 g) was added. The mixture was stirred at room temperature for 1 hour, and then water was added to the mixture. It was acidified with 10% hydrochloric acid and extraction with chloroform was conducted. The extract was washed with saturated saline and dried over sodium sulfate, and the solvent was distilled off under reduced pressure. The residue thus obtained was purified by silica gel column chromatography (Wako Gel C-200, 100 g). Elution with chloroform gave N-methoxycarbonyl-3-hydroxy-4-methoxyaniline (4.1 g).

IR $\nu_{max}$CHCl$_3$ (cm$^{-1}$): 3530, 3430, 1735.

$^1$H-NMR (CDCl$_3$, 100 MHz) δ:3.75 (3H, s), 3.85 (3H, s), 5.69 (1H, br s), 6.52 (1H, br s) 6.76∼7.00 (3H, m).

FD-MS (m/z): 198 (M+ +1).

The N-methoxycarbonyl-3-hydroxy-4-methoxyaniline (34.0 g) was dissolved in dimethylformamide (200 ml). Potassium carbonate (29.0 g) and trans-crotyl chloride (32.2 g) were added to the solution, and the mixture was stirred at room temperature for 5 hours. Water was added to the reaction mixture, and extraction was carried out with ethyl acetate. The extract was washed with saturated saline and dried over sodium sulfate, and the solvent was distilled off under reduced pressure. The crude crystal thus obtained was recrystallized from ethyl acetate-n-hexane to obtain N-methoxycarbonyl-3-(2-trans-butenyl)oxy-4-methoxyaniline (39.5 g).

M.p. 110°-111° (recrystallized from ethyl acetate-n-hexane).

IR $\nu_{max}$CHCl$_3$ (cm$^{-1}$): 3440, 1730.

$^1$H-NMR (CDCl$_3$, 100 MHz) δ:1.69∼1.80 (3H, m), 3.76 (3H, s), 3.83 (3H, s), 4.46∼4.58 (2H, m), 5.73∼5.89 (2H, m), 6.41 (1H, br s), 6.75∼6.83 (2H, m), 7.13 (1H, br s).

FD-MS (m/z): 251 (M+).

The N-methoxycarbonyl-3-(2-trans-butenyl)oxy-4-methoxyaniline (14.4 g) was suspended in N,N-dimethylaniline (75 ml), and the suspension was heated under reflux under a stream of argon for 1.5 hours, poured into 10% hydrochloric acid and extracted with chloroform. The extract was washed with saturated saline, and the solvent was distilled off under reduced pressure. The residue thus obtained was purified by silica gel column chromatography (Wako Gel C-200, 300 g). Elution with a mixed solvent of n-hexane (80 parts) and ethyl acetate (20 parts) gave a crude phenol product (8.6 g). The crude product (5.1 g) was dissolved in dimethylformamide (30 ml). To this solution were added potassium carbonate (4.2 g) and benzyl bromide (3.7 g), and the mixture was stirred at room temperature for 3 hours. Water was poured into the reaction mixture, and extraction was conducted with ethyl acetate. The extract was washed with saturated saline and dried over sodium sulfate, and the solvent was distilled off under reduced pressure. The residue thus obtained was purified by silica gel column chromatography (Wako Gel C-200, 100 g). Elution with a mixed solvent of n-hexane (85 parts) and ethyl acetate (15 parts) gave N-methoxycarbonyl-3-benzyloxy-2-[3-(but-1-enyl)]-4-methoxyaniline (4.8 g).

IR $\nu_{max}$CHCl$_3$ (cm$^{-1}$): 3400, 1730.

$^1$H-NMR (CDCl$_3$, 100 MHz) δ:1.25 (3H, d, J=6.4 Hz), 3.71 (3H, s), 3.86 (3H, s), 4.12∼4.42 (1H, m), 4.97 (2H, s), 5.08∼5.28 (2H, m), 5.96 (1H, ddd, J=2.5 Hz, 10.5 Hz, 15.0 Hz), 6.68 (1H, br s), 6.83 (1H, d, J=9.1 Hz), 7.23∼7.50 (6H, m).

FD-MS (m/z): 342 (M+ +1).

The N-methoxycarbonyl-3-benzyloxy-2-[3-(but-1-enyl)]-4-methoxyaniline (5.8 g) was dissolved in methylene chloride (100 ml) and cooled to −70° C., and ozone was blown into the solution for 20 minutes. After blowing with nitrogen gas, dimethylsulfide (3 ml) was added, the dry ice-acetone bath was removed, and the mixture was stirred at room temperature for 20 hours. Toluenesulfonic acid (200 mg) was added to this solution. The mixture was stirred further for 10 hours, washed with saturated saline and dried over sodium sulfate, and the solvent was distilled off under reduced pressure. The residue was purified by silica gel column chromatography (Wako Gel C-200, 100 g). Elution with chloroform gave 4-benzyloxy-5-methoxy-1-methoxycarbonyl-3-methylindole (4.6 g).

M.p. 123.5°-124.5° (recrystallized from ethyl acetate-n-hexane).

IR $\nu_{max}$CHCl$_3$ (cm$^{-1}$): 1730.

$^1$H-NMR (CDCl$_3$, 100 MHz) δ:2.28 (3H, d, J=1.5 Hz), 3.91 (3H, s), 3.97 (3H, s), 5.12 (2H, s), 6.98 (1H, d, J=9.1 Hz), 7.15~7.55 (6H, m), 7.83 (1H, d, J=9.1 Hz); FD-MS (m/z): 325 (M+).

The 4-benzyloxy-5-methoxy-1-methoxycarbonyl-3-methylindole (5.3 g) was dissolved in methanol (60 ml). A solution of potassium hydroxide (40.0 g) in water (60 ml) was added to the solution, and the mixture was heated under reflux for 2 hours. The reaction mixture was poured into water, and chloroform extraction was conducted. The extract was washed with saturated saline and dried over sodium sulfate, and the solvent was distilled off under reduced pressure. The residue was purified by silica gel column chromatography (Wako Gel C-200, 100 g). Elution with chloroform gave 4-benzyloxy-5-methoxy-3-methylindole (4.3 g).

M.p. 60°-61° (recrystallized from ethyl acetate-n-hexane).

IR $\nu_{max}$CHCl$_3$ (cm$^{-1}$): 3480.

$^1$H-NMR (CDCl$_3$, 100 MHz) δ:2.38 (3H, d, J=1.2 Hz) 3.89 (3H, s), 5.15 (2H, s), 6.77~6.85 (1H, m), 6.89 (1H, d, J=8.5 Hz), 7.00 (1H, d, J=8.5 Hz), 7.26 (5H, m), 7.68 (1H, br s).

FD-MS (m/z): 267 (M+).

EXPERIMENTAL EXAMPLE 5

In a mixed solvent of methanol (9 ml) and chloroform (1 ml) was dissolved 5-benzyloxy-6-methoxy-4(1H)-quinolone (120 mg). To this solution was added 10% palladium-carbon (50 mg), and the mixture was stirred under a stream of hydrogen at room temperature for 2 hours. The catalyst was removed by filtration, and the filtrate was concentrated under reduced pressure. The crude product thus obtained was recrystallized from chloroform-methanol-n-hexane to obtain 5-hydroxy-6-methoxy-4(1H)-quinolone hydrochloride (a salt of compound 1, 73 mg).

M.p. 217°-219° (recrystallized from chloroform-methanol-n-hexane).

IR $\nu_{max}$KBr (cm$^{-1}$): 3450, 1620.

$^1$H-NMR (DMSO-d$_6$, 500 MHz) δ:3.80 (3H, s) 5.99 (1H, d, J=7.3 Hz), 6.93 (1H, d, J=8.6 Hz), 7.38 (1H, d, J=8.6 Hz), 7.93 (1H, d, J=7.3 Hz) 12.2 (br s, 1H).

$^{13}$C-NMR (DMSO-d$_6$, 125 MHz) δ:56.8, 105.2, 105.7, 113.8, 120.7, 134.9, 140.5, 140.6, 149.5, 182.2.

FD-MS (m/z): 191 (M+).

EXPERIMENTAL EXAMPLE 6

5-Benzyloxy-4-methoxy-3-methylindole (2.46 g) was subjected to the cleavage and re-cyclization reaction of the indole ring to obtain 6-benzyloxy-5-methoxy-4(1H)-quinolone (370 mg).

M.p. 180°-180° (recrystallized from chloroform-methanol-n-hexane).

IR $\nu_{max}$KBr (cm$^{-1}$): 3430, 1610.

$^1$H-NMR (CDCl$_3$—CD$_3$OD (4:1), 100 MHz) δ:3.98 (3H, s), 5.17 (2H, s), 6.23 (1H, d, J=7.1 Hz), 7.22 (1H, d, J=9.1 Hz), 7.35 (1H, d, J=9.1 Hz), 7.23~7.54 (5H, m), 7.68 (1H, d, J=7.1 Hz).

FD-MS (m/z): 281 (M+).

The 5-benzyloxy-4-methoxy-3-methylindole (2.46 g) as the starting material was a novel compound and was prepared in the following procedures.

3-Acetoxy-4-benzyloxybenzoic acid (14.4 g) was treated in the same manner as in the preparation of N-methoxycarbonyl-3-hydroxy-4-methoxyaniline in Experimental Example 4 to obtain N-methoxycarbonyl-4-benzyloxy-3-hydroxyaniline (11.8 g).

IR $\nu_{max}$CHCl$_3$ (cm$^{-1}$): 3540, 3440, 1730.

$^1$H-NMR (CDCl$_3$, 100 MHz) δ:3.73 (3H, s), 5.04 (2H, s), 5.75 (1H, s), 6.55 (1H, br s), 6.78~6.98 (3H, m), 7.31~7.46 (5H, m).

FD-MS (m/z): 273 (M+).

The N-methoxycarbonyl-4-benzyloxy-3-hydroxyaniline (36.0 g) was O-alkylated in the same manner as in the preparation of N-methoxycarbonyl-3-(2-trans-butenyl)oxy-4-methoxyaniline in Experimental Example 4 to obtain N-methoxycarbonyl-4-benzyloxy-3-(2-trans-butenyl)oxyaniline (34.8 g).

M.p. 83°-84° (recrystallized from ethyl acetate-n-hexane).

IR $\nu_{max}$CHCl$_3$ (cm$^{-1}$): 3440, 1730.

$^1$H-NMR (CDCl$_3$, 100 MHz) δ:1.65~1.78 (3H, m), 3.75 (3H, s), 4.47 (2H, m), 5.09 (2H, s), 5.71~5.91 (2H, m), 6.65 (1H, dd, J=1.4 Hz, 8.7 Hz), 6.81 (1H, d, J=8.7 Hz), 7.16 (1H, d, J=1.4 Hz), 7.23~7.52 (5H, m).

FD-MS (m/z): 327 (M+).

The N-methoxycarbonyl-4-benzyloxy-3-(2-trans-butenyl)oxyaniline (34.8 g) was subjected to Claisen rearrangement and O-methylation in the same manner as in the preparation of N-methoxycarbonyl-3-benzyloxy-2-[3-(but-1-enyl)]-4-methoxyaniline in Experimental Example 4 to give N-methoxycarbonyl-2-[3-(but-1-enyl)]-4-benzyloxy-3-methoxyaniline (7.4 g).

IR $\nu_{max}$CHCl$_3$ (cm$^{-1}$): 3400, 1730.

$^1$H-NMR (CDCl$_3$, 100 MHz) δ:1.38 (3H, d, J=7.4 Hz), 3.72 (3H, s), 3.82 (3H, s), 4.05~4.43 (1H, m), 5.08 (2H, s), 5.13~5.31 (2H, m), 6.14 (1H, ddd, J=2.5 Hz, 10.5 Hz, 15.0 Hz), 6.68 (1H, br s), 6.85 (1H, d, J=9.1 Hz), 7.25~7.51 (6H, m).

FD-MS (m/z): 341 (M+).

The N-methoxycarbonyl-2-[3-(but-1-enyl)]-4-benzyloxy-3-methoxyaniline (7.6 g) was subjected to ozone degradation and dehydration in the same manner as in the preparation of 4-benzyloxy-5-methoxy-1-methoxycarbonyl-3-methylindole in Experimental Example 4 to give 5-benzyloxy-4-methoxy-1-methoxycarbonyl-3-methylindole (4.7 g).

M.p. 56°-57° (recrystallized from ethyl acetate-n-hexane).

IR $\nu_{max}$CHCl$_3$ (cm$^{-1}$): 1730.

$^1$H-NMR (CDCl$_3$, 100 MHz) δ:2.39 (3H, d, J=1.2 Hz), 3.96 (3H, s), 5.13 (2H, s), 6.97 (1H, d, J=8.8 Hz), 7.17~7.54 (6H, m), 7.77 (1H, d, J=8.8 Hz).

FD-MS (m/z): 325 (M+).

The 5-benzyloxy-4-methoxy-1-methoxycarbonyl-3-methylindole (4.5 g) was hydrolyzed in the same manner as in the preparation of 4-benzyloxy-5-methoxy-3-methylindole in Experimental Example 4 to give 5-benzyloxy-4-methoxy-3-methylindole (3.4 g).

M.p. 101°-102° (recrystallized from ethyl acetate-n-hexane);

IR $\nu_{max}$CHCl$_3$ (cm$^{-1}$): 3490.

$^1$H-NMR (CDCl$_3$, 100 MHz) δ:2.47 (3H, d, J=1.1 Hz), 3.99 (3H, s), 5.11 (2H, s), 6.80~6.88 (1H, m), 6.91 (2H, s), 7.23~7.56 (5H, m), 7.68 (1H, br s).
FD-MS (m/z): 267 (M+).

EXPERIMENTAL EXAMPLE 7

6-Benzyloxy-5-methoxy-4(1H)-quinolone (120 mg) was debenzylated in the same procedures as in Experimental Example 5 to give 6-hydroxy-5-methoxy-4(1H)-quinolone hydrochloride (a salt of compound 2, 76 mg).
M.p. 191°-193° (recrystallized from chloroform-methanol-n-hexane).
IR ν$_{max}$KBr (cm$^{-1}$): 3450, 1605.
$^1$H-NMR (DMSO-d$_6$, 500 MHz) δ:3.75 (3H, s), 6.14 (1H, t, J=6.7 Hz), 7.31 (2H, br s), 7.88 (1H, dd, J=4.3 Hz, 6.7 Hz), 9.34 (1H, br s).
$^{13}$C-NMR (DMSO-d$_6$, 125 MHz) δ:61.3, 107.9, 115.0, 119.8, 123.3, 135.3, 138.7, 143.4, 146.7, 174.2.
FD-MS (m/z): 191 (M+).

EXPERIMENTAL EXAMPLE 8

3,4-Dimethoxyaniline (3.0 g) and diethyl ethoxymethylenemalonate (5.1 g) were subjected to condensation and ring closure in the same manner as in Experimental Example 1 to give 6,7-dimethoxy-3-ethoxycarbonyl-4(1H)-quinolone (2.2 g).
The 6,7-dimethoxy-3-ethoxycarbonyl-4(1H)-quinolone (1.0 g) was dissolved in methanol (15 ml), and the solution was heated under reflux together with a 10% aqueous solution of NaOH (10 ml) for 2 hours. The mixture was acidified with a 10% aqueous solution of HCl, and the precipitate thus obtained was washed with water and acetone in sequence to give a carboxylic acid (830 mg).
The carboxylic acid (820 mg) was suspended in diphenyl ether (30 ml), and the mixture was heated under reflux at 280° C. under a stream of argon for 3 hours. After the mixture was left to cool to room temperature, it was purified by silica gel column chromatography (Wako Gel C-200, 50 g). Elution with a mixed solvent of chloroform (90 parts) and methanol (10 parts) gave 6,7-dimethoxy-4(1H)-quinolone (compound 6, 480 mg).
M.p. 119.5°-122.5°.
$^1$H-NMR (100 MHz, DMSO-d$_6$) 3.83 (3H, s), 3.86 (3H, s), 5.93 (1H, d, J=7.3 Hz), 6.95 (1H, s), 7.43 (1H, s), 7.68-7.85 (1H, m), 11.53 (1H, br s).

EXPERIMENTAL EXAMPLE 9

The 6,7-dimethoxy-3-ethoxycarbonyl-4(1H)-quinolone (2.3 g) was dissolved in dimethylformamide (46 ml). Potassium carbonate (1.1 g) and methyl iodide (2.0 ml) were added to the solution. The mixture was stirred at room temperature for 15 hours, and the solvent was distilled off. Methanol (30 ml) and a 10% aqueous solution of NaOH (20 ml) were added to the residue, and the mixture was heated under reflux for 1 hour. After acidification of the mixture with a 10% aqueous solution of HCl, the precipitate was collected by filtration, washed with acetone and dried to give a carboxylic acid (1.24 g). The carboxylic acid (0.95 g) was suspended in diphenyl ether (30 ml) and heated under reflux under a stream of argon at 280° C. for 6 hours. After the mixture was left to cool, the carboxylic acid deposited as the starting material was filtered, and the filtrate was concentrated and purified by silica gel column chromatography (Wako Gel C-200, 100 g). Elution with a mixed solvent of chloroform (50 parts) and acetone (50 parts) gave 6,7-dimethoxy-1-methyl-4(1H)-quinolone (compound 13, 390 mg).
M.p. 169.0°-173.0°.
$^1$H-NMR (100 MHz, CDCl$_3$) 3.79 (3H, s), 3.99 (3H, s), 4.00 (3H, s), 6.18 (1H, d, J=7.7 Hz), 6.67 (1H, s), 7.41 (1H, d, J=7.7 Hz), 7.77 (1H, s).

EXPERIMENTAL EXAMPLE 10

2-Amino-5-chlorobenzophenone (3.0 g) and diethyl ethoxymethylenemalonate (3.3 g) were reacted in the same manner as in Experimental Example 1 to give 8-benzoyl-6-chloro-3-ethoxycarbonyl-4(1H)-quinolone (2.1 g). The compound (1.4 g) was dissolved in methanol (24 ml). A 10% aqueous solution of NaOH (16 ml) was added to the solution, and the mixture was heated under reflux for 1 hour. After acidification of the mixture with a 10% aqueous solution of HCl, the precipitate was collected by filtration, washed with water and dried to give a carboxylic acid (1.2 g). The carboxylic acid (1.2 g) was suspended in diphenyl ether (30 ml), and the suspension was heated under reflux under a stream of argon at 280° C. for 3 hours. After the reaction mixture was left to cool, a mixed solvent of ether (50 parts) and n-hexane (50 parts) was added, and the crude crystal thus obtained was collected by filtration and recrystallized from chloroform-methanol-n-hexane to give 8-benzoyl-6-chloro-4(1H)-quinolone (compound 18, 0.6 g).
M.p. 193.0°-196.0°.
$^1$H-NMR (100 MHz, DMSO-d$_6$) 6.21 (1H, d, J=7.3 Hz), 7.50~8.00 (7H, m), 8.30 (1H, d, J=2.5 Hz), 11.66 (1H, s).

EXPERIMENTAL EXAMPLE 11

5-Phenyl-o-anisidine (3.0 g) and diethyl ethoxymethylenemalonate (3.9 g) were reacted in the same manner as in Experimental Example 1 to give 3-ethoxycarbonyl-8-methoxy-5-phenyl-4(1H)-quinolone (850 mg) (compound 37).
M.p. 234.0°-237.0°.
$^1$H-NMR (500 MHz, DMSO-d$_6$) 1.21 (3H, t, J=7.0 Hz), 4.04 (3H, s), 4.14 (2H, q, J=7.0 Hz), 7.00 (1H, d, J=8.6 Hz), 7.15~7.35 (6H, m), 8.30 (1H, s), 11.72 (1H, s).

EXPERIMENTAL EXAMPLE 12

A variety of compounds according to the present invention were prepared by the production methods described below. The measurements of the physico-chemical properties of these compounds are listed in Table 1.
Furthermore, a variety of compounds according to the present invention other than those described below were also prepared, and their physico-chemical properties were measured. The results are also listed in Table 1.

1) Compound 10

3,4-Diethoxyaniline (3.7 g) and diethyl ethoxymethylenemalonate (5.3 g) were reacted in the same manner as in Experimental Example 1 to obtain 6,7-diethoxy-3-ethoxycarbonyl-4(1H)-quinolone (4.3 g). The compound (3 g) was subjected to hydrolysis and decarboxylation in the same manner as in Experimental Example 2 to obtain 6,7-diethoxy-4(1H)-quinolone (compound 10, 1.9 g).

2) Compound 17

6,7-Dimethoxy-4(1H)-quinolone (0.5 g) was dissolved in dimethylformamide (10 ml). 60% Sodium hydride (130 mg) and 4-methoxybenzyl bromide (0.42 ml) were added to the solution, and the mixture was stirred at room temperature for 15 hours. Water was added to the mixture, and extraction was conducted with ethyl acetate. The extract was washed with water and dried over sodium sulfate, and the solvent was distilled off under reduced pressure. The residue was purified by silica gel column chromatography (Wako Gel C-200, 30 g). Elution with a mixed solvent of chloroform (90 parts) and methanol (10 parts) gave 6,7-dimethoxy-1-(4-methoxybenzyl)-4(1H)-quinolone (compound 17, 0.39 g).

3) Compound 20

4-Methoxy-2-methylaniline (3.0 g) and diethyl ethoxymethylenemalonate (5.7 g) were reacted in the same manner as in Experimental Example 1 to obtain 3-ethoxycarbonyl-6-methoxy-8-methyl-4(1H)-quinolone (3.4 g). The compound (2.0 g) was subjected to hydrolysis and decarboxylation in the same manner as in Experimental Example 2 to obtain 6-methoxy-8-methyl-4(1H)-quinolone (compound 20, 0.7 g).

4) Compound 26

4-Benzyloxy-2-methoxyaniline (2.9 g) and diethyl ethoxymethylenemalonate (2.7 g) were reacted in the same manner as in Experimental Example 1 to obtain 6-benzyloxy-3-ethoxycarbonyl-8-methoxy-4(1H)-quinolone (3.5 g). The compound (2.0 g) was subjected to hydrolysis and decarboxylation in the same manner as in Experimental Example 8 to obtain 6-benzyloxy-8-methoxy-4(1H)-quinolone (compound 26, 1.0 g).

5) Compound 30

4-Methoxy-2-methylsulfenylaniline (1.5 g) and diethyl ethoxymethylenemalonate (1.9 g) were reacted in the same manner as in Experimental Example 1 to obtain 3-ethoxycarbonyl-6-methoxy-8-methylsulfenyl-4(1H)-quinolone (2.1 g). The compound (1.3 g) was subjected to hydrolysis and decarboxylation in the same manner as in Experimental Example 2 to obtain 6-methoxy-8-methylsulfenyl-4(1H)-quinolone (compound 30, 0.95 g).

6) Compound 36

2-Methoxy-5-methylaniline (3.0 g) and diethyl ethoxymethylenemalonate (5.7 g) were reacted in the same manner as in Experimental Example 1 to obtain 3-ethoxycarbonyl-8-methoxy-5-methyl-4(1H)-quinolone (compound 36, 5.3 g).

7) Compound 49

4-Ethoxy-3-methoxyaniline (2.6 g) and diethyl ethoxymethylenemalonate (3.4 g) were reacted in the same manner as in Experimental Example 1 to obtain 6-ethoxy-3-ethoxycarbonyl-7-methoxy-4(1H)-quinolone (2.5 g). The compound (2.3 g) was ethylated with potassium carbonate (3.3 g) and ethyl iodide (6.1 g) in the same manner as in Experimental Example 9 to obtain 6-ethoxy-3-ethoxycarbonyl-1-ethyl-7-methoxy-4(1H)-quinolone (1.8 g). This compound (1.4 g) was hydrolyzed in the same manner as in Experimental Example 9 to obtain a carboxylic acid (1.2 g), which was then decarboxylated in the same manner as in Experimental Example 9 to obtain 6-ethoxy-1-ethyl-7-methoxy-4(1H)-quinolone (compound 49, 210 mg).

8) Compound 51

3-Hydroxy-4-methoxyaniline (3.0 g) and diethyl ethoxymethylenemalonate (5.6 g) were heated at a temperature of 100°-110° for 30 minutes, and dimethylformamide (24 ml) was added to this mixture. Further, potassium carbonate (4.47 g) and i-propyl bromide (2.43 ml) were added to the mixture, and the whole mixture was stirred at 60° for 15 hours. The precipitate was filtered off, and the filtrate was concentrated and purified by silica gel column chromatography (Wako Gel C-200, 150 g). Elution with a mixed solvent of n-hexane (75 parts) and ethyl acetate (25 parts) gave a diester derivative (3.0 g). The product (3.0 g) was suspended in diphenyl ether (30 ml), and the suspension was stirred at 250°-260° for 9 hours. After the reaction mixture was left to cool, it was purified by silica gel column chromatography (Wako Gel C-200, 150 g). Elution with a mixed solvent of chloroform (90 parts) and methanol (10 parts) gave 7-i-propoxy-6-methoxy-4(1H)-quinolone (compound 51, 690 mg).

9) Compound 52

3-Hydroxy-4-methoxyaniline (3.0 g) and diethyl ethoxymethylenemalonate (5.6 g) were condensed in the same manner as in the preparation of compound 51. The condensation product was next O-n-butylated with potassium carbonate (4.5 g) and n-butyl bromide (2.8 ml) in the same manner as above and heated in diphenyl ether to obtain 7-n-butoxy-6-methoxy-4(1H)-quinolone (compound 52, 1.65 g).

10) Compound 58

7-Ethoxy-6-methoxy-4(1H)-quinolone (compound 62, 0.68 g) was dissolved in dimethylformamide (14 ml). Potassium carbonate (640 mg) and ethyl iodide (0.3 ml) were added to the solution, and the mixture was stirred at room temperature for 4 hours. The precipitate was removed by filtration, and the filtrate was purified by silica gel column chromatography (Wako Gel C-200, 50 g). Elution with a mixed solvent of chloroform (90 parts) and methanol (10 parts) gave 7-ethoxy-1-ethyl-6-methoxy-4(1H)-quinolone (compound 58, 0.4 g).

11) Compound 62

3-Hydroxy-4-methoxyaniline (0.64 g) and diethyl ethoxymethylenemalonate (1.20 g) were stirred at 115° for 30 minutes. Dimethylformamide (9.6 ml), potassium carbonate (960 mg) and ethyl iodide (0.44 ml) were added to the mixture, and the whole mixture was stirred at room temperature for 20 hours. The precipitate was removed by filtration, and the filtrate was concentrated and purified by silica gel column chromatography (Wako Gel C-200, 25 g) to give diethyl (3-ethoxy-4-methoxyanilino)methylenemalonate (1.5 g). The product was suspended in diphenyl ether (19.5 ml), and the suspension was stirred at 250°-260° for 6 hours. After the reaction mixture was left to cool down to room temperature, ether was added to the mixture and the precipitate was collected by filtration. It was purified by silica gel column chromatography (Wako Gel C-200, 35 g) to give 7-ethoxy-6-methoxy-4(1H)-quinolone (compound 62, 280 mg).

12) Compound 67

3-Chloroaniline (5.0 g) and diethyl ethoxymethylenemalonate (10.2 g) were reacted in the same manner as in Experimental Example 1 to obtain 7-chloro-3-ethoxycarbonyl-4(1H)-quinolone (13.0 g). This compound (5.0 g) was hydrolyzed in the same manner as in Experimental Example 2 to obtain a carboxylic acid (4.2 g). This acid derivative (4.2 g) was dissolved in pyridine (40 ml), piperazine (5.2 g) was added to the solution, and the mixture was heated under reflux for 48 hours. The solvent was removed by distillation, and the residue was purified by column chromatography (Wako Gel C-200, 100 g). Elution with a mixed solvent of chloroform (90 parts) and methanol (10 parts) gave 7-piperazinyl-4(1H)-quinolone (compound 67, 3.3 g).

13) Compound 68

7-Ethoxy-3-ethoxycarbonyl-6-methoxy-4(1H)-quinolone (2.6 g) was subjected to N-n-butylation with potassium carbonate (1.4 g) and n-butyl bromide (1.4 ml) in the same manner as in Experimental Example 9, hydrolysis and decarboxylation to obtain 1-n-butyl-7-ethoxy-6-methoxy-4(1H)-quinolone (compound 68, 3.0 g).

14) Compound 69

7-Ethoxy-3-ethoxycarbonyl-6-methoxy-4(1H)-quinolone (2.6 g) was subjected to N-i-butylation with potassium carbonate (1.4 g) and i-butyl bromide (1.4 ml) in the same manner as in Experimental Example 9, hydrolysis and decarboxylation to obtain 7-ethoxy-1-isobutyl-6-methoxy-4(1H)-quinolone (compound 69, 1.3 g).

15) Compound 71

2-Amino-5-chlorotoluene (4.0 g) and diethyl ethoxy methylenemalonate (7.3 g) were reacted in the same manner as in Experimental Example 1 to obtain 6-chloro-3-ethoxycarbonyl-8-methyl-4(1H)-quinolone (6.6 g). The compound (3.0 g) was hydrolyzed and decarboxylated in the same manner as in Experimental Example 2 to obtain 6-chloro-8-methyl-4(1H)-quinolone (compound 71, 1.25 g).

16) Compound 72

3-Hydroxy-4-methoxyaniline (3.0 g) and diethyl ethoxymethylenemalonate (5.6 g) were heated at 130° for 1 hour. Dimethylformamide (45 ml), potassium carbonate (4.5 g) and transcrotyl bromide (2.7 ml) were then added to the mixture, and the whole mixture was stirred for 15 hours. The precipitate was removed by filtration, and the filtrate was concentrated and purified by silica gel column chromatography (Wako Gel C-200, 200 g). Elutin with a mixed solvent of n-hexane (80 parts) and ethyl acetate (20 parts) gave an O-crotyl derivative (8.1 g). This derivative was dissolved in diphenyl ether (82 ml), and the solution was heated at 240° for 4 hours. After the reaction mixture was left to cool, it was purified by silica gel column chromatography (Wako Gel C-200, 250 g). Elution with a mixed solvent of chloroform (10 parts) and methanol (1 part) gave 8-(2-trans-butenyl)-7-hydroxy-6-methoxy-4(1H)-quinolone (compound 72, 0.3 g).

17) Compound 76

4-Ethoxy-2-methoxyaniline (2.3 g) and diethyl ethoxymethylenemalonate (3.0 g) were reacted in the same manner as in Experimental Example 1 to give 6-ethoxy-3-ethoxycarbonyl-8-methoxy-4(1H)-quinolone (compound 76, 1.7 g).

18) Compound 77

6-Ethoxy-3-ethoxycarbonyl-8-methoxy-4(1H)-quinolone (1.5 g) was N-ethylated with potassium carbonate (2.1 g) and ethyl iodide (4.0 g) in the same manner as in Experimental Example 9 to give 6-ethoxy-3-ethoxycarbonyl-1-ethyl-8-methoxy-4(1H)-quinolone (compound 77, 1.4 g).

19) Compound 78

2-Ethoxy-4-methoxyaniline (2.2 g) and diethyl ethoxymethylenemalonate (2.9 g) were reacted in the same manner as in Experimental Example 1 to give 8-ethoxy-3-ethoxycarbonyl-6-methoxy-4(1H)-quinolone (2.9 g). The compound (1.5 g) was N-ethylated with potassium carbonate (2.1 g) and ethyl iodide (4.0 g) in the same manner as in Experimental Example 9 to give 8-ethoxy-3-ethoxycarbonyl-1-ethyl-6-methoxy-4(1H)-quinolone (compound 78, 1.3 g).

20) Compound 84

2-Amino-5-diethylaminotoluene (5.4 g) and diethyl ethoxymethylenemalonate (6.5 g) were reacted in the same manner as in Experimental Example 1 to give 6-diethylamino-3-ethoxycarbonyl-8-methyl-4(1H)-quinolone (compound 84, 5.4 g).

21) Compound 85 p-Ethylaniline (5.0 g) and diethyl ethoxymethylenemalonate (10.7 g) were reacted in the same manner as in Experimental Example 1 to give 3-ethoxycarbonyl-6-ethyl-4(1H)-quinolone (3.6 g). The compound (2.8 g) was N-ethylated with potassium carbonate (2.3 g) and ethyl iodide (2.1 g) in the same manner as in Experimental Example 9 to give 1,6-diethyl-3-ethoxycarbonyl-4(1H)-quinolone (compound 85, 1.55 g).

22) Compound 92

3-Hydroxy-4-methoxyaniline (10.0 g) and diethyl ethoxymethylenemalonate (17.0 g) were condensed in the same manner as in the preparation of compound 72. The condensation product was O-ethylated with potassium carbonate (15.0 g) and ethyl iodide (7.0 ml) and then heated in diphenyl ether (70 ml) at a temperature of 240°-250° for 3 hours. After the mixture was left to cool, ether was added to the mixture. The resulting precipitate was collected by filtration, washed with water and dried to give 7-ethoxy-3-ethoxycarbonyl-6-methoxy-4(1H)-quinolone (10.2 g). The compound (5.0 g) was subjected to N-methylation and hydrolysis in the same manner as in Experimental Example 9 to obtain 3-carboxyl-7-ethoxy-6-methoxy-1-methyl-4(1H)-quinolone (compound 92, 4.4 g).

23) Compound 94

2-Acetyl-4,5-dimethoxyaniline (300 mg) and 2-furoyl chloride (260 mg) were reacted in the same manner as in the preparation of compound 95 to obtain N-(2-furoyl)-2-acetyl-4,5-dimethoxyaniline (440 mg). The compound (380 mg) and potassium t-butoxide (740 mg) were reacted in the same manner as in the preparation of compound 95 to obtain 6,7-dimethoxy-2-(2-furyl)-4(1H)-quinolone (compound 94, 30 mg).

24) Compound 95

2-Acetyl-4,5-dimethoxyaniline (2.0 g) was dissolved in tetrahydrofuran (50 ml), and to the mixture were added triethylamine (2.2 g) and dimethylaminopyridine (400 mg), and then a solution of cyclopropylcarbonyl chloride (1.7 g) in tetrahydrofuran (5 ml). The mixture was stirred at room temperature for 3 hours. After the addition of a 10% aqueous solution of potassium hydroxide, the mixture was stirred and extraction was conducted with chloroform. The extract was washed with saturated saline and dried over sodium sulfate, and the solvent was distilled off under reduced pressure. The residue was purified by silica gel column chromatography (Wako Gel C-200, 50 g). Elution with a mixed solvent of n-hexane (60 parts) and ethyl acetate (40 parts) gave N-cyclopropylcarbonyl-2-acetyl-4,5-dimethoxyaniline (2.5 g). This amide product (1.0 g) was suspended in t-butanol (50 ml), and potassium t-butoxide (2.1 g) was added to the suspension, and the mixture was heated under reflux for 15 hours. After the mixture was left to cool, extraction was conducted with a mixed solvent of chloroform (90 parts) and methanol (10 parts). The extract was washed with saturated saline and dried over sodium sulfate, and the solvent was distilled off under reduced pressure. The residue was purified by silica gel column chromatography (Wako Gel C-200, 30 g). Elution with a mixed solvent of chloroform (97 parts) and methanol (3 parts) gave 2-cyclopropyl-6,7dimethoxy-4(1H)-quinolone (compound 95, 580 mg).

25) Compound 97

N-Ethyl-2-acetylaniline (580 mg) was dissolved in dimethylformamide (20 ml). To this solution were added 60% sodium hydride (213 mg) and then 2-thenoyl chloride (780 mg), and the mixture was stirred at room temperature for 1 hour. Solid ammonium chloride was added to the mixture, and stirring was continued for 15 minutes. Extraction was conducted with ethyl acetate. The extract was washed with a 10% aqueous solution of potassium hydroxide and saturated saline in sequence and dried over sodium sulfate, and the solvent was distilled off under reduced pressure. The residue was purified by silica gel column chromatography (Wako Gel C-200, 20 g). Elution with a mixed solvent of n-hexane (70 parts) and ethyl acetate (30 parts) gave N-ethyl-N'-(2-thenoyl)-2-acetylaniline (610 mg). The compound (610 mg) was subjected to ring closure with potassium to-butoxide (1.25 g) as in the preparation of compound 101 to obtain 1-ethyl-2-(2-thienyl)-4(1H)-quinolone (compound 97, 510 mg).

26) Compound 98

2-Acetyl-5-ethoxy-4-metoxyaniline (550 mg), cyclopropylcarbonyl chloride (410 mg) and triethylamine (530 mg) were reacted in the same manner as in the preparation of compound 95 to give N-cyclopropylcarbonyl-2-acetyl-5-ethoxy-4-methoxyaniline (740 mg). The compound (600 mg) and potassium t-butoxide (1.18 g) were reacted in the same manner as in the preparation of compound 95 to obtain 2-cyclopropyl-7-ethoxy-6-methoxy-4(1H)-quinolone (compound 98, 330 mg).

27) Compound 100

2-Acetylaniline (2.0 g) and 2-thenoyl chloride (3.2 g) were condensed in the same manner as in the preparation of compound 95 to obtain N-(2-thenoyl)-2-acetylaniline (3.1 g). The compound (2.0 g) and potassium t-butoxide (9.1 g) were reacted in the same manner as in the preparation of compound 95 to obtain 2-(2-thienyl)-4(1H)-quinolone (compound 100, 310 mg).

28) Compound 101

N-Ethyl-2-acetyl-5-ethoxy-4-methoxyaniline (300 mg) was reacted with triethylamine (260 mg), dimethylaminopyridine (100 mg) and 2-furoyl chloride (250 mg) in the same manner as in the preparation of compound 95 to obtain N-ethyl-N'-(2-furoyl)-2-acetyl-5-ethoxy-4-methoxyaniline (390 mg).

This amide (330 mg) was dissolved in t-butanol (20 ml). To this solution was added potassium t-butoxide (335 mg), and the mixture was stirred at room temperature for 1 hour. Water was added to the mixture, and extraction was conducted with a mixed solvent of chloroform (90 parts) and methanol (10 parts). The extract was washed with saturated saline and dried over sodium sulfate, and the solvent was distilled off under reduced pressure. The residue was purified by silica gel column chromatography (Wako Gel C-200, 20 g) to give 7-ethoxy-1-ethyl-2-(2-furyl)-6-methoxy-4(1H)-quinolone (compound 101, 270 mg).

29) Compound 102

N-Ethyl-2-acetyl-5-ethoxy-4-methoxyaniline (300 mg), 2-thenoyl chloride (280 mg) triethylamine (260 mg) and dimethylaminopyridine (100 mg) were reacted in the same manner as in the preparation of compound 95 to obtain N-etnyl-N'-(2-thenoyl)-2acetyl-5-ethoxy-4-methoxyaniline (440 mg). The compound (370 mg) was reacted with potassium t-butoxide (360 mg) in the same manner as in the preparation of compound 101 to obtain 7-ethoxy-1-ethyl-6-methoxy-2-(2-thienyl)-4(1H)-quinolone (compound 102, 310 mg).

30) Compound 103

N-Allyl-2-acetyl-5-ethoxy-4-methoxyaniline (600 mg), cyclopropylcarbonyl chloride (380 mg) and triethylamine (490 mg) were reacted in the same manner as in the preparation of compound 95 to obtain N-allyl-N'-cyclopropylcarbonyl-2-acetyl-5-ethoxy-4-methoxyaniline (740 mg). The compound (1.22 g) and potassium t-butoxide (1.30 g) were reacted in the same manner as in the preparation of compound 101 to obtain 1-allyl-2-cyclopropyl-7-ethoxy-6-methoxy-4(1H)-quinolone (compound 103, 1.0 g).

31) Compound 104

N-Cyclopropylcarbonyl-2-acetyl-4,5-dimethoxyaniline (260 mg) was dissolved in dimethylformamide (15 ml), and the solution was heated to a temperature of 50°-60°. To this solution were added 60% sodium hydride (60 mg) and p-methoxybenzyl chloride (230 mg), and the whole mixture was stirred at the same temperature as above for 1 hour. After the mixture was left to cool, solid ammonium chloride was added and the mixture was stirred for 15 minutes. Extraction was conducted with ethyl acetate. The extract was washed with saturated saline and dried over sodium sulfate, and the solvent was distilled off under reduced pressure. The residue was purified by silica gel column chromatography (Wako Gel C-200, 20 g). Elution with a mixed solvent of n-hexane (70 parts) and ethyl acetate (30 parts) gave N-(4-methoxybenzyl)-N'-cyclopropylcarbonyl-2-acetyl-4,5-dimethoxyaniline (390 mg). The compound (350 mg) was reacted with potassium t-butoxide (310 mg) in the same manner as in the preparation of compound 101 to obtain 2-cyclopropyl-6,7-dimethoxy-1-(4-methoxybenzy)-4(1H)-quinolone (compound 104, 180 mg).

32) Compound 108

The compound 109 (0.70 g) was dissolved in dimethylformamide (10.5 ml). To this solution were added potassium carbonate (0.40 g) and ethyl iodide (0.19 ml), and the mixture was stirred at 30° for 23 hours. After the solvent was removed, the residue was purified by silica gel column chromatography (Wako Gel C-200, 28 g). Elution with a mixed solvent of chloroform (80 parts) and acetone (20 parts) gave 1-ethyl-3-{1-[4-(2-methoxyphenyl)piperazinyl]carbonyl}-6-methyl-4(1H)-quinolone (compound 108, 0.52 g).

33) Compound 109

3-Ethoxycarbonyl-6-methyl-4(1H)-quinolone (1.00 g) and 2-methoxyphenylpiperazine (1.25 g) were suspended in pyridine (3 ml), and the mixture was heated under reflux for 22 hours. The solvent was removed by distillation, and the residue was purified by silica gel column chromatography (Wako Gel C-200, 90 g). Elution with a mixted solvent of chloroform (60 parts) and acetone (40 parts) gave 3-{1-[4-(2-methoxyphenyl)-piperazinyl]carbonyl}-6-methyl-4(1H)-quinolone (compound 109, 0.80 g).

34) Compound 112

N-Cyclopropylcarbonyl-2-acetyl-5-ethoxy-4-methoxyaniline (150 mg), 60% sodium hydride (40 mg) and p-methoxybenzyl bromide (180 mg) were reacted in the same manner as in the preparation of compound 104 to obtain N-(4-methoxybenzyl)-N'-cyclopropylcarbonyl-2-acetyl-5-ethoxy-4-methoxy-aniline (160 mg). This compound (90 mg) and potassium t-butoxide (130 mg) were reacted in the same manner as in the preparation of compound 101 to obtain 2-cyclopropyl-7-ethoxy-6-methoxy-1-(4-methoxybenzyl)-4(1H)-quinolone (compound 112, 35 mg).

35) Compound 113

N-Ethyl-2-acetylaniline (300 mg), sodium hydride (110 mg) and cyclopropylcarbonyl chloride (290 mg) were reacted in the same manner as in the preparation of compound 97 to obtain N-ethyl-N'-cyclopropylcarbonyl-2-acetylaniline (400 mg). This compound (360 mg) and potassium t-butoxide (520 mg) were reacted with each other in the same manner as in the preparation of compound 101 to obtain 2-cyclopropyl-1-ethyl-4(1H)-quinolone (compound 113, 330 mg).

36) Compound 114

N-Ethyl-2-acetyl-5-ethoxy-4-methoxyaniline (300 mg), 60% sodium hydride (150 mg) and nicotinic acid chloride hydrochloride (340 mg) were reacted in the same manner as in the preparation of compound 97 to obtain N-ethyl-N'-(3-pyridine)carbonyl-2-acetyl-5-ethoxy-4-methoxyaniline (320 mg). This compound (300 mg) and potassium t-butoxide (490 mg) were reacted in the same manner as in the preparation of compound 101 to obtain 7-ethoxy-1-ethyl-6-methoxy-2-(3-pyridyl)-4(1H)-quinolone (compound 114, 260 mg).

37) Compound 115

2-Acetyl-5-n-butoxy-4-methoxyaniline (320 mg), 60% sodium hydride (81 mg) and cyclopropylcarbonyl chloride (296 mg) were reacted in the same manner as in the preparation of compound 97 to obtain N-cyclopropylcarbonyl-2-acetyl-5-n-butoxy-4-methoxyaniline (360 mg). This compound (250 mg) and potassium t-butoxide (460 mg) were reacted with each other in the same manner as in the preparation of compound 95 to obtain 7-n-butoxy-2-cyclopropyl-6-methoxy-4(1H)-quinolone (compound 115, 90 mg).

38) Compound 116

N-Allyl-2-acetyl-5-ethoxy-4-methoxyaniline (240 mg), 60% sodium hydride (58 mg) and 2-thenoyl chloride (210 mg) were reacted in the same manner in the preparation of compound 97 to obtain N-allyl-N'-(2-thenoyl)-2-acetyl-5-ethoxy-4-methoxyaniline (340 mg). This compound (310 mg) and potassium t-butoxide (484 mg) were reacted in the same manner as in the preparation of compound 101 to obtain 1-allyl-7-ethoxy-6-methoxy-2-(2-thienyl)-4(1H)-quinolone (compound 116, 180 mg).

39) Compound 117

N-(2-trans-butenyl)-2-acetyl-5-ethoxy-4-methoxyaniline (150 mg), 60% sodium hydride (34 ) and cyclopropylcarbonyl chloride (100 mg) were reacted in the same manner as in the preparation of compound 97 to obtain N-(2-trans-butenyl)-N'-cyclopropylcarbonyl-2-acetyl-5-ethoxy-4-methoxyaniline (90 mg). This compound (60 mg) and potassium t-butoxide (101 mg) were reacted in the same manner as in the preparation of compound 101 to obtain 1-(2-trans-butenyl)-2-cyclopropyl-7-ethoxy-6-methoxy-4(1H)-quinolone (compound 117, 25 mg).

40) Compound 118

N-Ethyl-2-acetyl-5-n-butoxy-4-methoxyaniline (300 mg), 60% sodium hydride (68 mg) and 2-furoyl chloride (231 mg) were reacted in the same manner as in the preparation of compound 97 to obtain N-ethyl-N'-(2-furoyl)-2-acetyl-5-n-butoxy-4-methoxyaniline (330 mg). This compound (330 mg) and potassium t-butoxide (514 mg) were reacted in the same manner as in the preparation of compound 101 to obtain 7-n-butoxy-1-ethyl-2-(2-furyl)-6-methoxy-4(1H)-quinolone (compound 118, 260 mg).

41) Compound 119

2-Acetyl-4-ethoxy-5-methoxyaniline (490 mg), triethylamine (1.0 ml) and cyclopropylcarbonyl chloride (0.25 ml) were reacted in the same manner as in the preparation of compound 95 to give N-cyclopropylcarbonyl-2-acetyl-4-ethoxy-5-methoxyaniline (420 mg). This compound (380 mg) and potassium t-butoxide (770 mg) were reacted in the same manner as in the preparation of compound 95 to obtain 2-cyclopropyl-6-ethoxy-7-methoxy-4(1H)-quinolone (compound 119, 80 mg).

TABLE 1

[Structure: benzoyl group with R1", R2", R3", R4" substituents on benzene ring, attached via C=O to a pyridine/quinoline ring with N-R5" and R6"]

| Compound | R1" | R2" | R3" | R4" | R5" | R6" | mp (°C.) | 1H-NMR |
|---|---|---|---|---|---|---|---|---|
| (7) | H | H | H | CN | H | H | 255.0~259.5 | (100MHz, DMSO-d6)6.16(1H, d, J=7.8Hz), 7.45(1H, t, J=7.8Hz), 7.70~7.95(1H, m), 8.21(1H, dd, J=7.8Hz, 1.5Hz), 8.37(1H,dd, J=7.8Hz, 1.5Hz), 11.76(1H, br s) |
| (8) | CN | H | H | H | H | H | 262.0~268.5 | (100MHz, DMSO-d6)6.14(1H, d, J=7.8Hz), 7.70~7.80(3H, m), 7.99 (1H, d, J=7.3Hz), 12.10(1H, br s) |
| (9) | H | N(Et)2 | H | Me | H | H | 213.0~218.5 | (100MHz, DMSO-d6)1.10(6H, t, J=6.7Hz), 2.46(3H, s), 3.38(4H, q, J=6.7Hz), 5.97(1H, d, J=7.3Hz) 7.07(2H, s), 7.68(1H, d, J=7.3Hz) |
| (10) | H | OEt | OEt | H | H | H | 157.0~161.0 | (100MHz, DMSO-d6)1.38(3H, t, J=6.8Hz), 1.41(3H, t, J=6.8Hz), 4.08(2H, q, J=6.8Hz), 4.10(2H, q, J=6.8Hz), 5.96(1H, d, J=7.3Hz), 6.96(1H, s), 7.45(1H, s), 7.65~7.90(1H, m), 11.57(1H, br s) |
| (11) | H | OMe | H | OMe | H | H | 219.5~222.0 (dec.) | (100MHz, DMSO-d6)3.81(3H, s), 3.96(3H, s), 5.99(1H, d, J=7.3Hz), 6.84(1H, d, J=2.2Hz), 7.05(1H, d, J=2.2Hz), 7.67(1H, m) |
| (12) | H | OAc | H | H | H | H | 228~231.0 | (100MHz, DMSO-d6)2.30(3H, s), 6.05(1H, d, J=7.7Hz), 7.42(1H, dd, J=2.6Hz, 8.9Hz), 7.61(1H, d, J=2.6Hz), 7.76(1H, d, J=8.9Hz), 7.93(1H, d, J=7.7Hz) |
| (13) | H | OAc | H | H | Ac | H | 235.0~235.5 | (100MHz, CDCl3)2.38(3H, s), 2.48 (3H, s), 7.37(1H, d, J=5.0Hz), 7.50(1H, dd, J=2.6Hz, 9.1Hz), 7.70(1H, d, J=2.6Hz), 8.15(1H, d, J=9.1Hz), 8.89(1H, d, J=5.0Hz) |
| (15) | H | H | H | OMe | Me | H | 138.0~139.5 | (100MHz, DMSO-d6)3.91(3H, s), 4.04(3H, s), 5.99(1H, d, J=7.8Hz), 7.27(1H, d, J=5.5Hz), 7.29(1H, d, J=4.1Hz), 7.78(1H, dd, J=4.1Hz, 5.5Hz), 7.80(1H, d, J=7.8Hz) |
| (16) | H | OMe | H | OMe | Et | H | 67.0~70.0 | (100MHz, CDCl3)1.39(3H, t, J=7.1Hz), 3.92(3H, s), 3.94(3H, s), 4.46(2H, q, J=7.1Hz), 6.26(1H, d, J=7.7Hz), 6.77(1H, d, J=2.9Hz), 7.41(1H, d, J=7.7Hz), 7.52(1H, d, |

TABLE 1-continued

| Compound | R1″ | R2″ | R3″ | R4″ | R5″ | R6″ | mp (°C.) | 1H-NMR |
|---|---|---|---|---|---|---|---|---|
| (17) | H | OMe | OMe | H | CH2—C6H4—OMe | H | | (100MHz, CDCl3)3.77(3H, s)3.78(3H, s), 3.95(3H, s), 5.23(2H, s), 6.28(1H, d, J=7.6Hz), 6.68(1H, s), 6.85(1H, d, J=8.8Hz), 7.10 (1H, d, J=8.8Hz), 7.60(1H, d, J=7.6Hz), 7.77(1H, s) J=2.9Hz) |
| (19) | OEt | H | H | OEt | H | H | 268.0~271.0 | (100MHz, DMSO-d6)1.33(3H, t, J=7.1Hz), 1.42(3H, t, J=7.1Hz), 3.97(2H, q, J=7.1Hz), 4.16(2H, q, J=7.1Hz), 5.97(1H, d, J=7.3Hz), 6.65(1H, d, J=8.7Hz), 7.11(1H, d, J=8.7Hz), 7.66(1H, d, J=7.3Hz), 10.90(1H, m) |
| (20) | H | OMe | H | Me | H | H | 186.0~187.5 | (500MHz, DMSO-d6)2.47(3H, s), 3.81(3H, s), 6.05(1H, d, J=7.3Hz), 7.15(1H, d, J=3.0Hz), 7.37(1H, d, J=3.0Hz), 7.78(1H, d, J=7.3Hz), 11.15(1H, m) |
| (21) | H | H | H | iPr | H | H | 161.5~164.0 | (500MHz, DMSO-d6)1.28(3H, s), 1.29(3H, s), 3.44(1H, m), 6.08 (1H, d, J=6.4Hz), 7.30(1H, t, J=7.6Hz), 7.58(1H, d, J=7.6Hz), 7.84(1H, d, J=6.4Hz), 8.98(1H, d, J=7.6Hz), 11.18(1H, br s) |
| (22) | Me | H | H | OMe | H | H | 164.0~165.0 | (500MHz, DMSO-d6)2.71(3H, s), 3.94(3H, s), 5.96(1H, d, J=6.7Hz), 6.90(1H, d, J=7.9Hz), 7.07(1H, d, J=7.9Hz), 7.63(1H, t, J=6.7Hz), 11.05(1H, br s) |
| (23) | OMe | H | H | Ph | H | H | >297.0 | (500MHz, DMSO-d6)4.01(3H, s), 5.91(1H, d, J=7.3Hz), 6.90(1H, d, J=7.9Hz), 7.15~7.30(6H, m), 7.69 (1H, t, J=7.3Hz), 11.20(1H, br s) |
| (24) | H | H | OMe | OMe | H | H | 57.0~58.0 | (100MHz, CDCl3)3.99(3H, s), 4.01(3H, s), 6.23(1H, d, J=7.6Hz), 7.02(1H, d, J=8.7Hz), 7.50~7.70 (1H, m)8.08(1H, d, J=8.7Hz) |
| (25) | OMe | H | H | SMe | H | H | 204.5~205.5 | (100MHz, CDCl3)2.40(3H, s), 4.01(3H, s), 6.47(1H, d, J=6.4Hz) |

TABLE 1-continued

| Compound | $R^{1''}$ | $R^{2''}$ | $R^{3''}$ | $R^{4''}$ | $R^{5''}$ | $R^{6''}$ | mp (°C.) | 1H-NMR |
|---|---|---|---|---|---|---|---|---|
| (26) | H | PhCH$_2$O | H | OMe | H | H | 181.0~182.0 | 6.73(1H, d, J=8.5Hz), 7.58(1H, d, J=8.5Hz), 7.84~8.10(1H, m) (100MHz, CDCl$_3$)3.93(3H, s), 5.13 (2H, s), 6.31(1H, d, J=2.3Hz), 6.78(1H, d, J=2.3Hz), 7.29~7.70 (7H, m), 9.27(1H, br s) |
| (27) | H | OMe | OMe | OMe | H | H | 72.0~73.0 | (100MHz, CDCl$_3$)3.93(3H, s), 3.98 (3H, s), 4.05(3H, s), 6.30(1H, d, J=7.3Hz), 7.54(1H, s), 7.65~7.83 (1H, m), 10.49(1H, br s) |
| (28) | OH | H | OMe | OMe | H | H | 210~212.0 | (100MHz, DMSO-d$_6$)3.80(3H, s), 5.95(1H, d, J=7.1Hz), 6.16(1H, d, J=3.0Hz), 6.38(1H, d, J=3.0Hz), 7.92(1H, d, J=7.1Hz), 12.02(1H, s), 14.72(1H, s) |
| (29) | H | SO$_2$Me | H | OMe | Et | H | 142.0~143.0 | (100MHz, CDCl$_3$)1.44(3H, t, J=7.3Hz), 3.12(3H, s), 4.06(3H, s), 4.49(2H, q, J=7.3Hz), 6.32(1H, d, J=7.9Hz), 7.46(1H, d, J=7.9Hz), 7.56(1H, d, J=2.0Hz), 8.63(1H, d, J=2.0Hz) |
| (30) | H | OMe | H | SMe | H | H | 137.0~138.0 | (100MHz, CDCl$_3$)2.48(3H, s), 3.90 (3H, s), 6.33(1H, d, J=7.6Hz), 7.42(1H, d, J=2.9Hz), 7.69~7.77 (2H, m) |
| (31) | H | H | H | CN | H | CO$_2$Et | 192.0~196.5 | (100MHz, DMSO-d$_6$)1.29(3H, t, J=7.3Hz), 4.25(2H, q, J=7.3Hz), 7.56(1H, dd, J=7.8Hz, 7.3Hz), 8.26(1H, dd, J=7.3Hz, 1.5Hz), 8.43(1H, s)8.44(1H, dd, J=7.8Hz, 1.5Hz), 12.30(1H, br s) |
| (32) | H | OMe | OMe | H | Me | CO$_2$Me | 234.0~240.0 | (100MHz, DMSO-d$_6$)3.74(3H, s), 3.86(3H, s), 3.92(3H, s), 3.96 (3H, s), 7.08(1H, s), 7.60(1H, s), 8.58(1H, s) |
| (33) | H | Me | H | H | Et | CO$_2$Et | 188.0~188.5 | (100MHz, CDCl$_3$(1.42(3H, t, J=7.1Hz), 1.54(3H, t, J=7.3Hz), 2.48(3H, s), 4.25(2H, q, J=7.3Hz), 4.41(2H, q, J=7.1Hz), 7.35(1H, d, J=8.5Hz), 7.52(1H, dd, J=8.5 Hz, 2.2Hz), 8.36(1H, d, J=8.5Hz), 8.48(1H, s) |

TABLE 1-continued

[Structure: phenyl ring with substituents R1″, R2″, R3″, R4″ connected via C(=O) to a pyridine ring with N-R5″ and R6″]

| Compound | R1″ | R2″ | R3″ | R4″ | R5″ | R6″ | mp (°C.) | 1H-NMR |
|---|---|---|---|---|---|---|---|---|
| (34) | H | OMe | OEt | H | Et | CO2Et | 158.0~161.0 | (100MHz, DMSO-d6)1.29(3H, t, J = 7.1Hz), 1.37(3H, t, J = 7.1Hz), 1.42(3H, t, J = 7.1Hz), 3.86(3H, s), 4.23(2H, q, J = 7.1Hz), 4.24 (2H, q, J = 7.1Hz), 4.41(2H, q, J = 7.1Hz), 7.09(1H, s), 7.62(1H, s), 8.55(1H, s) |
| (35) | H | H | H | OMe | H | CO2Et | 235.5~238.0 | (100MHz, DMSO-d6)1.26(3H, t, J = 7.3Hz), 4.00(3H, s), 4.20(2H, q, J = 7.3Hz), 7.31(1H, d, J = 3.4Hz) 7.32(1H, d, J = 5.4Hz), 7.70(1H, dd, J = 3.4Hz, 5.4Hz), 8.34(1H, d, J = 6.8Hz), 11.89(1H, br s) |
| (36) | Me | H | H | OMe | H | CO2Et | 178.0~183.0 | (100MHz, DMSO-d6)1.27(3H, t, J = 7.1Hz), 2.70(3H, s), 3.96(3H, s), 4.19(2H, q, J = 7.1Hz), 7.03(1H, d, J = 7.8Hz), 7.19(1H, d, J = 7.8Hz), 8.24(1H, d, J = 6.8Hz), 11.55(1H, br s) |
| (38) | H | H | OMe | OMe | Et | CO2Et | 115.0~116.0 | (100MHz, CDCl3)1.37(3H, t, J = 7.1Hz), 1.48(3H, t, J = 7.0Hz), 3.90(3H, s), 4.00(3H, s), 4.38 (2H, q, J = 7.0Hz), 4.47(2H, q, J = 7.1Hz), 7.10(1H, d, J = 9.1Hz), 8.33(1H, d, J = 9.1Hz), 8.37(1H, s) |
| (39) | H | SOMe | H | OMe | Et | CO2Et | 192.0~193.0 | (100MHz, CDCl3)1.42(3H, t, J = 7.3Hz), 1.48(3H, t, J = 7.0Hz), 2.78(3H, s), 4.10(3H, s), 4.40 (2H, q, J = 7.3Hz), 4.59(2H, q, J = 7.0Hz), 7.70(1H, d, J = 2.1Hz), 8.18(1H, d, J = 2.1Hz), 8.41(1H, s) |
| (40) | H | SO2Me | H | OMe | Et | CO2Et | 195.0~196.0 | (100MHz, CDCl3)1.41(3H, t, J = 7.0Hz), 1.49(3H, t, J = 7.0Hz), 3.11(3H, s), 4.08(3H, s), 4.40 (2H, q, J = 7.0Hz), 4.58(2H, q, J = 7.0Hz), 7.61(1H, d, J = 2.3Hz), 8.40(1H, s), 8.66(1H, d, J = 2.3Hz) |
| (41) | H | OMe | OMe | H | H | CH2OH | 275.0~285.0 (dec.) | (100MHz, DMSO-d6)3.83(3H, s), 3.86(3H, s), 4.41(2H, br s), 4.90(1H, br s), 7.01(1H, s), 7.46(1H, s), 7.76(1H, s), 11.80 (1H, br s) |

TABLE 1-continued

[Structure: substituted phenyl ketone with R1", R2", R3", R4" on ring; C(=O)–CH=C(R6")–N(R5") group]

| Compound | R1" | R2" | R3" | R4" | R5" | R6" | mp (°C.) | 1H-NMR |
|---|---|---|---|---|---|---|---|---|
| (42) | H | OMe | OMe | H | Me | CH2OH | 229.5~233.0 | (100MHz, DMSO-d6)3.85(3H, s), 3.87(3H, s), 3.97(3H, s), 4.40 (2H, s), 7.01(1H, s), 7.55(1H, s), 7.87(1H, s) |
| (43) | OMe | OMe | OMe | H | Me | CO2H | 207.0~209.5 | (100MHz, DMSO-d6)3.82(3H, s), 3.83(3H, s), 4.40(6H, s), 7.06 (1H, s), 8.90(1H, s), 16.20(1H, br s) |

| Compound | R1'' | R2'' | R3'' | R4'' | R5'' | R6'' | R7'' | Y | mp (°C.) | 1H-NMR |
|---|---|---|---|---|---|---|---|---|---|---|
| (44) | H | H | H | Ac | H | H | H | O | 152.0~155.0 | (500MHz, DMSO-d6) 2.75(3H, s), 6.15(1H, d, J=7.6Hz), 7.46(1H, t, J=7.9Hz), 7.98(1H, d, J=7.6Hz), 8.41(1H, dd, J=7.9 Hz, 1.2Hz), 8.48(1H, dd, J=7.9Hz, 1.2Hz), 12.25(1H, br s). |
| (45) | H | CH2CN | H | H | H | H | H | O | 208.0~209.0 | (500MHz, DMSO-d6) 4.16(2H, s), 6.04(1H, d, J=7.3 Hz), 7.56(1H, d, J=8.5Hz), 7.60 (1H, dd, J=8.5Hz, 1.8Hz), 7.92 (1H, m), 8.09(1H, br s), 11.81 (1H, br s). |
| (46) | H | OMe / MeO (vinyl substituent) | H | H | H | H | H | O | 204.0~205.0 | (500MHz, DMSO-d6) 3.77(3H, s), 3.83(3H, s), 6.05 (1H, d, J=7.3Hz), 6.85(1H, dd, J=8.9Hz, 3.1Hz), 6.97(1H, d, J=8.9Hz), 7.30(1H, d, J=3.1Hz), 7.41(1H, d, J=16.1Hz), 7.44(1H, d, J=16.1Hz), 7.55(1H, d, J=8.6 Hz), 7.89(1H, d, J=7.3Hz), 7.91 (1H, dd, J=8.6Hz, 1.8Hz), 8.20 (1H, dd, J=1.8Hz), 11.84(1H, s). |
| (47) | H | MeO | H | EtO | H | H | H | O | 178.0~180.0 | (100MHz, CDCl3) 1.50(3H, t, J=7.1Hz), 3.88(3H, s), 4.19(2H, q, J=7.1Hz), 6.31 (1H, d, J=7.3Hz), 6.69(1H, d, J=2.6Hz), 7.30(1H, d, J=2.9Hz), 7.63(1H, d, J=7.3Hz), 9.14(1H, br s). |
| (48) | H | EtO | MeO | H | H | H | H | O | 260.0~265.0 (dec.) | (100MHz, CDCl3-CD3OD(4:1)) 1.51(3H, t, J=7.1Hz), 3.94(3H, s), 4.21(2H, q, J=7.1Hz), 6.25 (1H, d, J=7.3Hz), 6.80(1H, s), 7.56(1H, d, J=7.3Hz), 7.63(1H, s). |
| (49) | H | EtO | MeO | H | Et | H | H | O | 157.0~159.0 | (100MHz, CDCl3) 1.48(3H, t, J=7.3Hz), 1.51(3H, q, J=6.8Hz), 3.99(3H, s), 4.13(2H, q, J=6.8Hz), 4.23(2H, q, J=7.3Hz), 6.20(1H, d, J=7.6Hz), 6.75(1H, s), |

-continued

| Compound | R1'' | R2'' | R3'' | R4'' | R5'' | R7'' | R6'' | Y | mp (°C.) | 1H-NMR |
|---|---|---|---|---|---|---|---|---|---|---|
| (50) | H | H | Me | Me | Et | H | H | O | 83.0~83.5 | (100MHz, CDCl3) 1.30(3H, t, J=7.1Hz), 2.44(3H, s), 2.48(3H, s), 4.23(2H, q, J=7.1Hz), 6.37(1H, d, J=7.6Hz), 7.22(1H, d, J=8.1Hz), 7.46(1H, d, J=7.6Hz), 7.61(1H, J=7.6Hz), 8.20(1H, d, J=8.1Hz), 7.81(1H, s) |
| (51) | H | MeO | iPro | H | H | H | H | O | 188.0~190.5 | (100MHz, CDCl3) 1.30(6H, d, J=6.0Hz), 3.87(3H, s), 4.48(1H, sept, J=6.0Hz), 6.36(1H, d, J=7.2Hz), 7.16(1H, s), 7.69(1H, s), 7.81(1H, d, J=7.2Hz) |
| (52) | H | MeO | nBuO | H | H | H | H | O | 192.5~195.5 | (100MHz, CDCl3) 0.90(3H, t, J=7.1Hz), 1.20~2.00 (4H, m), 3.87(3H, s), 3.93(3H, s), 6.28(1H, d, J=7.3Hz), 7.06(1H, s), 7.69(1H, s), 7.71 (1H, d, J=7.3Hz) |
| (53) | H | MeO | ~~O~~ (allyloxy) | H | H | H | H | O | 110.5~112.0 | (100MHz, CD3OD) 3.66(2H, d, J=5.4Hz), 3.97(3H, s), 4.80~5.10(2H, m), 6.03(1H, m), 6.29(1H, d, J=7.2Hz), 7.57 (1H, s), 7.80(1H, d, J=7.2Hz), 7.87(1H, s) |
| (54) | H | MeO | dioxolanyl-CH2O | H | H | H | H | O | 211.0~212.5 | (100MHz, CDCl3) 3.93(3H, s), 3.80-4.20(6H, m), 5.35(1H, t, J=3.9Hz), 6.46(1H, d, J=7.0Hz), 7.34(1H, s), 7.68(1H, s), 7.83(1H, d, J=7.0Hz) |
| (55) | H | MeO | MeOCH2O | H | H | H | H | O | 194.0~196.0 | (100MHz, CDCl3) 3.39(3H, s), 3.89(3H, s), 3.60~4.20(4H, m), 6.36(1H, d), 7.21 (1H, s), 7.69(1H, s), 7.79(1H, d, J=7.1Hz) |

-continued

| Compound | R1'' | R2'' | R3'' | R4'' | R5'' | R7'' | R6'' | Y | mp (°C.) | 1H-NMR |
|---|---|---|---|---|---|---|---|---|---|---|
| (56) | H | MeO | MeO-O (methylenedioxy with R2'') | H | H | H | H | O | 214.5~220.5 | (100MHz, CD3OD) 3.34(3H, s), 3.98(3H, s), 5.50 (2H, s), 6.20(1H, d, J=7.6Hz), 7.19(1H, s), 7.67(1H, s), 7.97 (1H, d, J=7.6Hz) |
| (57) | H | H | Me | H | Et | H | H | O | 162.0~163.0 | (100MHz, CDCl3) 1.51(3H, t, J=7.1Hz), 2.54(3H, s), 4.26(2H, q, J=7.1Hz), 6.47 (1H, d, J=7.6Hz), 7.25(1H, d, J=8.8Hz), 7.28(1H, s), 7.73(1H, d, J=7.6Hz), 8.36(1H, d, J=8.8Hz) |
| (58) | H | MeO | EtO | H | Et | H | H | O | 138.0~139.5 | (100MHz, DMSO-d6) 1.34(3H, t, J=7.3Hz), 1.41(3H, t, J=7.3Hz), 3.84(3H, s), 4.00~4.20 (4H, m), 5.96(1H, d, J=7.6Hz), 7.02(1H, s), 7.55(1H, s), 7.85 (1H, d, J=7.6Hz) |
| (59) | H | Me | H | H | Et | H | H | O | 92.0~95.0 | (100MHz, DMSO-d6) 1.46(3H, t, J=7.2Hz), 2.45(3H, s), 4.16(2H, q, J=7.2Hz), 6.23 (1H, d, J=7.8Hz), 7.33(1H, d, J=8.8Hz), 7.48(1H, dd, J=8.8Hz, 2.0Hz), 7.52(1H, d, J=7.8Hz), 8.25 (1H, br s) |
| (60) | H | H | O-CH2-O (methylenedioxy) | H | Et | H | H | O | 143.0~145.5 | (100MHz, DMSO-d6) 1.47(3H, t, J=7.2Hz), 4.10(2H, q, J=7.2Hz), 6.08(2H, s), 6.22 (2H, d, J=7.7Hz), 6.84(1H, s), 7.44(1H, d, J=7.7Hz), 7.82(1H, s) |
| (61) | OH | H | H | Me | Et | H | H | O | 113.0~116.0 | (100MHz, DMSO-d6) 1.26(3H, t, J=7.1Hz), 2.60(3H, s), 4.42(2H, q, J=7.1Hz), 6.14 (1H, d, J=7.5Hz), 6.55(1H, d, J=8.6Hz), 7.38(1H, d, J=8.6Hz), 8.06(1H, d, J=7.5Hz), 15.37(1H, s) |
| (62) | H | MeO | EtO | H | H | H | H | O | 258.0~261.0 | (100MHz, DMSO-d6) 1.41(3H, t, J=7.0Hz), 3.83(3H, |

-continued

| Compound | R1'' | R2'' | R3'' | R4'' | R5'' | R6'' | R7'' | R6''' | Y | mp (°C.) | 1H-NMR |
|---|---|---|---|---|---|---|---|---|---|---|---|
| (63) | H | H | O-CH2-O (3,4-methylenedioxy) | | H | H | H | H | S | 209.0~213.0 | s), 4.10(2H, q, J=7.0Hz), 5.94 (1H, d, J=7.3Hz), 6.94(1H, s), 7.44(1H, s), 7.76(1H, d, J=7.3 Hz), 11.5(1H, m) |
| (64) | H | HO-CH2CH2- | H | H | Et | H | H | H | | | (100MHz, CDCl3) 1.56(3H, t, J=7.3Hz), 4.36(2H, q, J=7.3Hz), 6.18(2H, s), 7.00 (1H, s), 7.67(2H, s), 8.39(1H, s) |
| (65) | H | CO2Et | H | H | H | H | H | H | O | 190.0~193.0 | (500MHz, DMSO-d6) 2.50(2H, t, J=1.8Hz), 3.60~3.70 (2H, m), 4.65(1H, br s), 6.00, (1H, d, J=7.3Hz), 7.45(1H, d, J=8.6Hz), 7.51(1H, dd, J=8.6Hz, 1.8Hz), 7.84(1H, m), 7.90(1H, d, J=1.8Hz), 11.69(1H, br s) |
| (66) | Ph | H | H | MeO | H | H | H | H | O | 153.5~154.5 | (500MHz, DMSO-d6) 1.36(3H, t, J=7.3Hz), 4.35(2H, q, J=7.3Hz), 6.18(1H, d, J=7.3Hz), 7.65(1H, d, J=8.6Hz), 8.02(1H, d, J=7.3Hz), 8.16(1H, dd, J=8.6 Hz, 1.8Hz), 8.71(1H, d, J=1.8Hz), 12.2(1H, br s) |
| (67) | H | H | piperazinyl (N-NH) | H | Et | H | H | H | O | 84.0~85.0 | (500MHz, CDCl3) 1.43(3H, t, J=7.3Hz), 3.99(3H, s) 4.45(2H, q, J=7.3Hz), 6.12(1H, d, J=7.9Hz), 7.11(1H, d, J=7.5Hz), 7.20~7.40(6H, m) |
| (68) | H | H | H | H | H | H | H | H | O | 254.5~257.0 | (500MHz, DMSO-d6) 3.21~3.25(4H, m), 3.48~3.52 (4H, m), 5.88(1H, d, J=7.3Hz), 6.85 (1H, d, J=2.4Hz), 7.05(1H, dd, J= 8.6Hz, 2.4Hz), 7.73(1H, d, J=7.3 Hz), 7.91(1H, d, J=8.6Hz), 11.60 (1H, br s) |
| | H | MeO | EtO | H | nBu | H | H | H | O | 123.5~124.0 | (500MHz, CDCl3) 0.99(3H, t, J=7.3Hz), 1.38~1.44 (2H, m), 1.56(3H, t, J=6.7Hz), |

-continued

| Compound | R1'' | R2'' | R3'' | R4'' | R5'' | R6'' | R7'' | Y | mp (°C.) | 1H-NMR |
|---|---|---|---|---|---|---|---|---|---|---|
| (69) | H | MeO | EtO | H | iBu | | H | O | 162.0~165.0 | (500MHz, CDCl3) 1.00(6H, d, J=6.7Hz), 1.56(3H, t, J=7.3Hz), 2.20~2.30(1H, m), 3.85 (2H, d, J=7.3Hz), 4.00(3H, s), 4.19(2H, q, J=7.3Hz), 6.21(1H, d, J=7.3Hz), 6.72(1H, s), 7.40(1H, d, J=7.3Hz), 7.83(1H, s) |
| (70) | H | H | H | ⟨isopropyl⟩ | H | | H | O | 144.5~145.0 | (500MHz, DMSO-d6) 2.14(3H, s), 5.13(1H, s), 5.51 (1H, s), 6.07(1H, d, J=7.3Hz), 7.31 (1H, t, J=7.3Hz), 7.49(1H, d, J=7.3Hz), 7.80(1H, m), 8.07(1H, d, J=7.3Hz), 10.82(1H, s) |
| (71) | H | Cl | H | Me | H | | H | O | >295.0 | (500MHz, DMSO-d6) 2.51(3H, s), 6.10(1H, d, J=7.3 Hz), 7.56(1H, d, J=2.4Hz), 7.86 (1H, d, J=7.3Hz), 7.89(1H, d, J=2.4 Hz), 11.55(1H, s) |
| (72) | H | MeO | HO | ⟨CH2CH=CHMe⟩ | H | | H | O | 223.5~225.0 | (500MHz, DMSO-d6) 1.63(3H, d, J=6.1Hz), 3.46(2H, d, J=6.1Hz), 3.79(3H, s), 5.44(1H, dq, J=15.3Hz, 6.9Hz), 5.61 (1H, dt, J=15.3Hz, 6.7Hz), 6.04 (1H, d, J=7.3Hz), 7.24(1H, s), 7.85~7.95(1H, m), 11.40(1H, br s), 14.74(1H, s) |
| (73) | H | MeO | H | H | Et | | H | O | 86.0~86.5 | (500MHz, CDCl3) 1.48(3H, t, J=7.3Hz), 3.93(3H, s), 4.17(2H, q, J=7.3Hz), 6.25 (1H, d, J=7.9Hz), 7.29(1H, dd, J= 9.8Hz, 3.1Hz), 7.40(1H, d, J=9.8 Hz), 7.50(1H, d, J=7.3Hz), 7.87 |

-continued

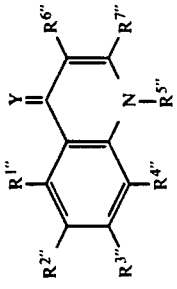

| Compound | R1″ | R2″ | R3″ | R4″ | R5″ | R6″ | R7″ | Y | mp (°C.) | 1H-NMR |
|---|---|---|---|---|---|---|---|---|---|---|
| (74) | H | EtO | H | H | Et | H | H | O | 118.5~119.0 | (1H, d, J=3.1Hz) (500MHz, CDCl3) 1.45(3H, t, J=7.3Hz), 1.49(3H, t, J=7.3Hz), 4.17(4H, q, J=7.3 Hz), 6.25(1H, d, J=7.6Hz), 7.28 (1H, dd, J=9.2Hz, 2.4Hz), 7.39 (1H, d, J=9.2Hz), 7.50(1H, d, J=7.6Hz), 7.85(1H, d, J=2.4Hz) |
| (75) | H | Et | H | H | Et | H | H | O | 74.5~75.0 | (500MHz, CDCl3) 1.30(3H, t, J=7.3Hz), 1.49(3H, t, J=7.3Hz), 2.78(2H, q, J=7.3Hz), 4.17(2H, q, J=7.3Hz), 6.27(1H, d, J=7.9Hz), 7.37(1H, d, J=9.2Hz), 7.51(1H, d, J=7.9Hz), 7.50~7.55 (1H, m), 8.31(1H, br s) |
| (76) | H | EtO | H | MeO | H | CO2Et | H | O | 208.0~210.0 | (100MHz, CDCl3) 1.42(3H, t, J=8.0Hz), 1.46(3H, t, J=7.0Hz), 3.98(3H, s), 4.15(2H, q, J=8.0Hz), 4.42(2H, q, J=7.0 Hz), 6.75(1H, d, J=2.5Hz), 7.28 (1H, d, J=2.5Hz), 8.72(1H, s) |
| (77) | H | EtO | H | MeO | Et | CO2Et | H | O | 131.0~132.0 | (100MHz, CDCl3) 1.34~1.53(9H, m), 3.94(3H, s), 4.16(2H, q, J=7.0Hz), 4.40(2H, q, J=7.3Hz), 4.53(2H, q, J=7.0Hz), 6.78(1H, d, J=2.6Hz), 7.63(1H, d, J=2.6Hz), 8.33(1H, s) |
| (78) | H | MeO | H | EtO | Et | CO2Et | H | O | 146.0~147.0 | (100MHz, CDCl3) 1.34~1.63(9H, m), 3.90(3H, s), 4.16(2H, q, J=7.0Hz), 4.40(2H, q, J=7.0Hz), 4.58(2H, q, J=7.0 Hz), 6.75(1H, d, J=2.9Hz), 7.63 (1H, d, J=2.9Hz), 8.33(1H, s) |

-continued

| Compound | R1'' | R2'' | R3'' | R4'' | R5'' | R7'' | R6'' | Y | mp (°C.) | 1H-NMR |
|---|---|---|---|---|---|---|---|---|---|---|
| (79) | EtO | H | H | MeO | H | H | CO2CH2CH2OEt | O | 182.0~183.0 | (100MHz, CDCl3) 1.21(3H, t, J=7.0Hz), 1.52(3H, t, J=7.0Hz), 3.58(2H, q, J=7.0Hz), 3.68~3.84(2H, m), 3.96(3H, s), 4.15(2H, q, J=7.0Hz), 4.41~4.58 (2H, m), 6.76(1H, d, J=9.1Hz), 7.01(1H, d, J=9.1Hz), 8.93(1H, br s) |
| (80) | H | H | H | MeO | H | H | CO2Et | S | 191.0~194.5 | (100MHz, DMSO-d6) 1.30(3H, t, J=7.1Hz), 4.03(3H, s), 4.26(2H, q, J=7.1Hz), 7.33(1H, dd, J=7.6Hz, 2.0Hz), 7.44(1H, t, J=7.6Hz), 8.00(1H, s), 8.27(1H, dd, J=7.6Hz, 2.0Hz) |
| (81) | H | H | Me | Me | Et | H | CO2Et | O | 110.0~111.0 | (100MHz, CDCl3) 1.36(3H, t, J=7.2Hz), 1.42(3H, t, J=7.0Hz), 2.43(3H, s), 2.48(3H, s), 4.31(2H, q, J=7.2Hz), 4.40 (2H, q, J=7.0Hz), 7.26(1H, d, J=7.9Hz), 8.28(1H, d, J=7.9Hz), 8.49(1H, s) |
| (82) | AcO | H | H | Me | Et | H | CO2Et | O | 119.5~120.0 | (100MHz, DMSO-d6) 1.24(3H, t, J=7.1Hz), 1.28(3H, t, J=7.1Hz), 2.28(3H, s), 2.67 (3H, s), 4.21(2H, q, J=7.1Hz), 4.45(2H, q, J=7.1Hz), 6.97(1H, d, J=8.4Hz), 7.58(1H, d, J=8.4Hz), 8.52(1H, s) |
| (83) | H | H | H | PhSO2 | H | H | CO2Et | O | 159.0~164.0 | (500MHz, DMSO-d6) 1.32(3H, t, J=6.7Hz), 4.28(2H, q, J=6.7Hz), 7.60~8.90(9H, m), 11.59(1H, br s) |
| (84) | H | N(Et)2 | H | Me | H | H | CO2Et | O | 139.5~141.0 | (500MHz, DMSO-d6) 1.11(6H, t, J=7.3Hz), 1.27(3H, t, J=7.3Hz), 2.48(3H, s), 3.30~3.50 (4H, m), 4.22(2H, q, J=7.3Hz), 7.08~7.19(2H, m), 8.25(1H, s), 11.53(1H, br s) |
| (85) | H | Et | H | H | Et | H | CO2Et | O | 146.0~146.5 | (500MHz, CDCl3) 1.29(3H, t, J=7.3Hz), 1.42(3H, t, |

-continued

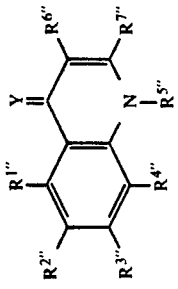

| Compound | R1'' | R2'' | R3'' | R4'' | R5'' | R7'' | R6'' | Y | mp (°C.) | 1H-NMR |
|---|---|---|---|---|---|---|---|---|---|---|
| (86) | H | EtO | MeO | H | Et | H | CO2H | O | 235.0~237.0 | (100MHz, CDCl3) 1.54(3H, t, J=7.3Hz), 2.77(2H, q, J=7.3Hz), 4.39(2H, q, J=7.3Hz), 7.38(1H, d, J=8.6Hz), 7.52(1H, dd, J=8.6Hz, 1.8Hz), 8.36(1H, d, J=1.8Hz), 8.46(1H, s) |
| (87) | Me | H | H | H | Et | H | CO2H | O | 200.5~204.5 | (100MHz, DMSO-d6) 1.54(3H, t, J=6.7Hz), 1.61(3H, t, J=7.0Hz), 4.06(3H, s, ), 4.16~4.48 (4H, m), 6.90(1H, s), 7.82(1H, s), 8.68(1H, s) |
| (88) | H | EtO | Me | Me | Et | H | CO2H | O | 282.5~283.5 | (100MHz, DMSO-d6) 1.40(3H, t, J=7.1Hz), 2.90(3H, s), 4.57(2H, q, J=7.1Hz), 7.40~8.00(3H, m), 9.01(1H, s), 15.65 (1H, s) |
| (89) | H | MeO | Me | Me | Me | H | CO2H | O | 282.5~283.0 | (100MHz, DMSO-d6) 1.48(6H, t, J=7.1Hz), 2.37(3H, s), 2.72(3H, s), 4.23(2H, q, J=7.1Hz), 4.51(2H, q, J=7.1Hz), 7.44(1H, s), 8.97(1H, s) |
| (90) | H | Me | H | H | Et | H | CO2H | O | 229.5~231.5 | (100MHz, DMSO-d6) 2.35(3H, s), 2.70(3H, s), 3.99 (3H, s), 4.29(3H, s), 7.46(1H, s), 8.94(1H, s) |
| (91) | Ph | H | H | MeO | H | H | CO2H | O | 195.5~196.5 | (500MHz, DMSO-d6) 1.42(3H, t, J=7.0Hz), 2.50(3H, s), 4.59(2H, q, J=7.0Hz), 7.79 (1H, dd, J=9.2Hz, 1.8Hz), 7.94 (1H, d, J=9.2Hz), 8.17(1H, br s), 9.01(1H, s), 15.33(1H, br s) |
| (92) | H | MeO | EtO | H | Me | H | CO2H | O | 271.0~276.0 | (500MHz, DMSO-d6) 4.10(3H, s), 7.20~7.40(6H, m), 7.50(1H, d, J=7.9Hz), 8.58(1H, m), 12.88(1H, br s), 15.25 (1H, br s) |
| (93) | H | MeO | EtO | H | nPr | H | CO2H | O | 203.0~ | (500MHz, DMSO-d6) 1.44(3H, t, J=6.7Hz), 3.92(3H, s), 4.09(3H, s), 4.29(2H, q, J=6.7Hz), 7.24(1H, s), 7.67(1H, s), 8.90(1H, s), 15.78(1H, br s) (500MHz, CDCl3) |

-continued

| Compound | R1'' | R2'' | R3'' | R4'' | R5'' | R7'' | R6'' | Y | mp (°C.) | 1H-NMR |
|---|---|---|---|---|---|---|---|---|---|---|
| (94) | H | MeO | MeO | H | H | (furyl) | H |  | 204.0 | 1.05(3H, t, J=7.3Hz), 1.60(3H, t, J=7.3Hz), 1.94~2.03(2H, m), 4.03 (3H, s), 4.18~4.32(4H, m), 6.88 (1H, s), 7.84(1H, s), 8.67(1H, s) |
| (95) | H | MeO | MeO | H | H | (cyclopropyl) | H | O | 281.0~283.0 (dec.) | (100MHz, CDCl$_3$—CD$_3$OD(3:1)) 4.00(6H, s), 6.59~6.66(1H, m), 6.66(1H, s), 7.11~7.18(1H, m), 7.13(1H, s), 7.62(1H, s), 7.60~7.71(1H, m) |
| (96) | H | H | H | H | H | (cyclopropyl) | H | O | >280 | (100MHz, CDCl$_3$—CD$_3$OD(5:1)) 0.86~1.22(4H, m), 1.75~2.01(1H, m), 3.91(3H, s), 3.94(3H, s), 5.86 (1H, s), 6.86(1H, s), 7.55(1H, s) |
| (97) | H | H | H | H | Et | (thienyl) | H | O | 221.0~223.0 | (100MHz, CDCl$_3$) 0.85~1.19(4H, m), 1.93~2.35(1H, m), 5.97(1H, s), 7.20~7.82(3H, m), 8.28~8.40(1H, m) |
| (98) | H | MeO | EtO | H | H | (cyclopropyl) | H | O | 169.0~171.0 | (100MHz, CDCl$_3$) 1.41(3H, t, J=7.0Hz), 4.23(2H, q, J=7.0Hz), 6.41(1H, s), 7.10~7.82 (6H, m), 8.44~8.57(1H, m) |
| (99) | PhCH$_2$O | MeO | H | H | H | (pyridyl) | H | O | >280 | (100MHz, CDCl$_3$—CD$_3$OS(4:1)) 0.86~1.15(4H, m), 1.51(3H, t, J= 7.0Hz), 1.70~2.01(1H, m), 4.13 (2H, q, J=7.0Hz), 5.88(1H, s), 6.87(1H, s), 7.58(1H, s) |
|  |  |  |  |  |  |  |  | O | 148.0~150.0 | (100MHz, CDCl$_3$) 4.06(3H, s), 5.34(2H, s), 7.15 (1H, s), 7.32~7.60(7H, m), 7.90 (1H, d, J=9.4Hz), 8.30~8.45(1H, m), 8.64(1H, dd, J=4.7Hz, 1.8Hz), 9.23~9.29(1H, m) |

-continued

| Compound | R1'' | R2'' | R3'' | R4'' | R5'' | R7'' | R6'' | Y | mp (°C.) | 1H-NMR |
|---|---|---|---|---|---|---|---|---|---|---|
| (106) | Me | H | H | MeO | H | H | ON—⟨piperidine⟩—Ph | O | 127.0~131.0 | (100MHz, CDCl$_3$) 2.83(3H, s), 3.97(3H, s), 1.60~4.50(9H, m), 6.91(1H, d, J=8.3 Hz), 7.01(1H, d, J=8.3Hz), 7.10~7.40(5H, m), 8.11(1H, s) |
| (107) | H | H | H | MeO | Me | H | ON—⟨piperazine⟩—CH$_2$-benzodioxole | O | — | (500MHz, CDCl$_3$) 2.59(4H, br s), 3.50~3.70(2H, m), 3.82(2H, br s), 4.14(3H, s), 3.94(3H, s), 5.94(2H, s), 6.74 (1H, d, J=7.9Hz), 6.78~6.80(1H, m), 6.90(1H, br s), 7.14~7.16 (1H, m), 7.33(1H, t, J=7.9Hz), 7.86(1H, s), 8.07(1H, dd, J=7.9Hz, 1.2Hz) |
| (108) | H | Me | H | H | Et | H | ON—⟨piperazine⟩—(2-MeO-C$_6$H$_4$) | O | 194.0~196.0 | (100MHz, CDCl$_3$) 1.53(3H, t, J=7.1Hz), 2.48(3H, s), 3.11~3.20(4H, m), 3.61~3.70 (2H, m), 3.87(3H, s), 3.95~4.05 (2H, m), 4.23(2H, q, J=7.1Hz), 6.76~7.16(4H, m), 7.33(1H, d, J=8.5Hz), 7.54(1H, dd, J=8.5Hz, 2.5Hz), 8.05(1H, s), 8.29(1H, br s) |
| (109) | H | Me | H | H | H | H | ON—⟨piperazine⟩—(2-MeO-C$_6$H$_4$) | O | 120.0~122.0 | (100MHz, CDCl$_3$) 2.39(3H, s), 2.88~3.28(4H, m), 3.48~4.00(4H, m), 3.83(3H, s), 6.80~7.10(4H, m), 7.31(1H, dd, J=8.5Hz), 2.5Hz), 7.49(1H, d,(J=8.5Hz), 8.00(1H, s), 8.13(1H, s) |
| (110) | H | MeO | MeO | H | Et | H | ON—⟨piperazine⟩—(4-NO$_2$-C$_6$H$_4$) | O | 297.0~299.0 | (100MHz, CDCl$_3$) 1.57(3H, t, J=7.0Hz), 3.42~4.05 (8H, m), 4.01(3H, s), 4.04(3H, s), 4.25(2H, q, J=7.0Hz), 6.83(2H, d, J=9.4Hz), 6.81(1H, s), 7.83 (1H, s), 8.02(1H, s), 8.12(2H, d, J=9.4Hz) |

-continued

| Compound | R1'' | R2'' | R3'' | R4'' | R5'' | R7'' | R6'' | Y | mp (°C.) | 1H-NMR |
|---|---|---|---|---|---|---|---|---|---|---|
| (111) | H | OMe | H | H | Et |  | H | O | oil | (500MHz, CDCl3)1.52(3H, t, J=7.3 Hz), 3.83(3H, s), 3.87(3H, S), 4.21(2H, q, J=7.3Hz), 6.37(1H, d, J=7.3Hz), 6.81(1H, dd, J=9.2Hz 3.1Hz), 6.85(1H, d, J=8.6Hz), 7.15(1H, d, J=3.1Hz), 7.22(1H, d, J=16.5Hz), 7.44(1H, d, J=9.2Hz), 7.55(1H, d, J=8.6Hz), 7.56(1H, d, J=16.5Hz), 7.89(1H, dd, J=8.6Hz, 1.8Hz), 8.57(1H, d, J=1.8Hz) |
| (112) | H | MeO | EtO | H |  | H | H | O | 180.0~182.0 | (100MHz, CDCl3) 0.83~1.11(4H, m), 1.42(3H, t, J=7.0Hz), 1.68~2.05(1H, m), 3.78(3H, s), 3.91(2H, q, J=7.0Hz) 3.97(3H, s), 5.62(2H, s), 6.22 (1H, s), 6.69(1H, s), 6.85(2H, d, J=9.1Hz), 7.02(2H, d, J=9.1Hz), 7.79(1H, s) |
| (113) | H | H | H | H | Et |  | H | O | 62.0~63.0 | (100MHz, CDCl3), 0.82~1.27(4H, m), 1.48(3H, t, J=7.0Hz), 1.77~2.15(1H, m), 4.55(2H, q, J=7.0Hz) 6.18(1H, s), 7.25~7.78(3H, m), 8.38~8.53(1H, m) |
| (114) | H | MeO | EtO | H | Et |  | H | O | 193.0~195.0 | (100MHz, CDCl3), 1.37(3H, t, J=7.0Hz), 1.64(3H, t, J=7.0Hz), 3.94~4.07(2H, m), 4.02(3H, s), 4.23(2H, q, J=7.0Hz), 6.16(1H, s), 6.90(1H, s), 7.40~7.58(1H, m), 7.71~7.92(1H, m), 7.87(1H, s), 8.68~8.86(1H, m), |
| (115) | H | MeO | "BuO | H | H | | H | O | 217.0~219.0 | (100MHz, DCD2) 0.74~2.10(14H, m), 3.80(3H, s), 3.84(2H, t, J=6.7 Hz), 5.93(1H, s), 7.05(1H, s), 7.63(1H, s) |

-continued

| Compound | R1'' | R2'' | R3'' | R4'' | R5'' | R6'' | R7'' | Y | mp (°C.) | 1H-NMR |
|---|---|---|---|---|---|---|---|---|---|---|
| (116) | H | MeO | EtO | H | allyl | H | 2-thienyl | O | 154.0~156.0 | (100MHz, CDCl₃), 1.53(3H, t, J=7.0Hz), 4.01(3H, s), 4.15(2H, q, J=7.0Hz), 4.66~4.81(2H, m), 4.98~5.52(2H, m), 5.81~6.19(1H, m), 6.43(1H, s), 6.87(1H, s), 7.05~7.17(1H, m), 7.24~7.31(1H, m), 7.43~7.53(1H, m), 7.83(1H, s) |
| (117) | H | MeO | EtO | H | 2-butenyl (Me) | H | cyclopropyl | O | 169.0~170.0 | (100MHz, CDCl₃), 0.81~1.15(4H, m), 1.53(3H, t, J=7.0Hz), 1.66~1.90(4H, m), 3.98(3H, s), 416 (2H, q, J=7.0Hz), 4.91~5.05(2H, m), 5.49~5.63(2H, m), 6.16(1H, s), 6.83(1H, s), 7.78(1H, s) |
| (118) | H | MeO | ⁿBuO | H | Et | H | 2-furyl | O | 113.0~114.0 | (100MHz, CDCl₃), 1.05(3H, t, J=6.8Hz), 1.50(3H, t, J=7.0Hz), 1.44~2.03(7H, m), 3.99(3H, s), 4.01~4.24(4H, m), 6.42(1H, s), 6.52~6.60(1H, m), 6.69~6.75(1H, m), 6.92(1H, s), 7.59~7.64(1H, m), 7.82(1H, s) |
| (119) | H | EtO | MeO | H | H | H | cyclopropyl | O | 288.0~289.5 | (100MHz, CDCl₃), 0.80~1.20(4H, m), 1.46(3H, t, J=6.9Hz), 1.60~2.00(1H, m), 3.88(3H, s), 4.13(2H, q, J=6.9Hz), 5.88(1H, s), 6.83(1H, s), 7.60 (1H, s) |

PHARMACOLOGICAL TEST

Test Method 1

The drug according to the present invention was evaluated with reference to the physiological activities by means of a method using an atrial muscle extirpated from a guinea pig.

Male guinea pigs having a body weight of 300–500 g were made swooned by striking his head and were bleeded to death. The heart was extirpated and the right and left atrial muscles were cut off. The tops of each atrial muscle were fixed with cerrefines. The muscle was suspended into an organ-bath in which a Krebs-Henseleit solution (at 32° C.) was filled, and a 95% $O_2$-5% $CO_2$ gas was flown through the bath. The left atrial muscle was stimulated electrically at a frequency of 1 Hz to stabilize the contracting force of the left atrial muscle. Then, the compounds according to the present invention represented by the general formulae were added to the organ-bath. As for the right atrial muscle, after the pulsation was stabilized, the compounds according to the present invention were added in the organ-bath in the same manner as described above.

The compounds according to the present invention represented by the aforementioned general formulae enhanced the left atrial muscle contracting force dependent on their concentrations. The drug concentrations for enhancing the left atrial muscle contracting force to the levels of 20%, 50% and 100%, respectively are listed in Table 2. $EC_{20}$, $EC_{50}$ and $EC_{100}$ indicate the molar concentration for enhancing the left atrial muscle contracting force to the levels of 20%, 50% and 100%, respectively. The enhancing rates of the pulsation of the right atrial muscle are also listed within parentheses. The minus values in parentheses indicate that the pulsation of the right atrial muscle is decreased.

As a control drug, theophylline (manufactured by Wako compounds according to the present invention.

TABLE 2

| Compound | $EC_{20}$ | $EC_{50}$ | $EC_{100}$ |
|---|---|---|---|
| (1) | $1.99 \times 10^{-4}$M (1.2%) | $3.98 \times 10^{-4}$M (3.6%) | $7.08 \times 10^{-4}$M (6.8%) |
| (2) | $4.90 \times 10^{-4}$M (0.6%) | $8.71 \times 10^{-4}$M (2.2%) | — |
| (3) | $7.08 \times 10^{-4}$M (0.8%) | $9.77 \times 10^{-4}$M (2.0%) | — |
| (4) | $1.00 \times 10^{-3}$M (0.7%) | — | — |
| (5) | $7.41 \times 10^{-4}$M (0.2%) | — | — |
| (6) | $1.00 \times 10^{-5}$M | $3.55 \times 10^{-5}$M | $2.34 \times 10^{-4}$M |
| (9) | $4.07 \times 10^{-5}$M (8.2%) | $8.71 \times 10^{-5}$M (15.3%) | $2.99 \times 10^{-4}$M (18.0%) |
| (10) | $1.88 \times 10^{-6}$M | $1.93 \times 10^{-5}$M | $1.16 \times 10^{-4}$M |
| (13) | $1.25 \times 10^{-5}$M (0.1%) | $8.81 \times 10^{-5}$M (1.2%) | $4.47 \times 10^{-4}$M (4.0%) |
| (17) | $4.47 \times 10^{-6}$M (−2.1%) | $3.00 \times 10^{-5}$M (−4.0%) | — |
| (18) | $1.00 \times 10^{-5}$M (0.2%) | $3.93 \times 10^{-5}$M (9.2%) | $1.15 \times 10^{-4}$M (12.2%) |
| (20) | $1.24 \times 10^{-5}$M (0.2%) | $5.89 \times 10^{-5}$M (1.8%) | $2.99 \times 10^{-4}$M (5.6%) |
| (26) | $6.38 \times 10^{-6}$M (0.1%) | $6.30 \times 10^{-5}$M (5.5%) | $3.05 \times 10^{-4}$M (8.7%) |
| (30) | $6.92 \times 10^{-6}$M | $7.85 \times 10^{-5}$M | $8.81 \times 10^{-4}$M |
| (32) | $4.07 \times 10^{-5}$M (0.1%) | $8.51 \times 10^{-5}$M (0.3%) | $2.82 \times 10^{-4}$M (0.4%) |
| (33) | $3.00 \times 10^{-5}$M (1.5%) | $7.67 \times 10^{-5}$M (1.7%) | $5.13 \times 10^{-4}$M (−7.1%) |
| (34) | $6.46 \times 10^{-6}$M (−3.2%) | $1.00 \times 10^{-4}$M (−8.5%) | — |
| (35) | $2.60 \times 10^{-5}$M (−1.2%) | $8.00 \times 10^{-5}$M (−2.0%) | $2.60 \times 10^{-4}$M (−3.7%) |
| (36) | $3.54 \times 10^{-6}$M (0.0%) | $2.57 \times 10^{-5}$M (3.6%) | $7.76 \times 10^{-5}$M (8.9%) |
| (37) | $1.58 \times 10^{-6}$M (−1.3%) | $7.50 \times 10^{-6}$M (−2.2%) | $3.72 \times 10^{-5}$M (−5.0%) |
| (39) | $1.35 \times 10^{-5}$M (−7.7%) | $6.76 \times 10^{-5}$M (−12.1%) | — |
| (40) | $4.57 \times 10^{-6}$M (−4.5%) | $3.63 \times 10^{-5}$M (−16.0%) | — |
| (44) | $<10^{-4}$M | $1.36 \times 10^{-4}$M | $7.76 \times 10^{-4}$M |
| (45) | $<10^{-4}$M | $2.74 \times 10^{-4}$M | $5.10 \times 10^{-4}$M |
| (46) | $4.57 \times 10^{-5}$M (−1.0%) | $1.62 \times 10^{-4}$M (3.5%) | — |
| (47) | $<10^{-4}$M | $<10^{-4}$M | $2.00 \times 10^{-4}$M |
| (48) | $1.26 \times 10^{-5}$M | $1.06 \times 10^{-4}$M | $6.46 \times 10^{-4}$M |
| (49) | $1.68 \times 10^{-5}$M (−2.5%) | $6.24 \times 10^{-5}$M (−1.0%) | $2.29 \times 10^{-4}$M (10.2%) |
| (51) | $2.00 \times 10^{-5}$M (6.2%) | $7.08 \times 10^{-5}$M (16.8%) | $1.00 \times 10^{-3}$M (16.5%) |
| (52) | $3.76 \times 10^{-5}$M (−1.0%) | $1.15 \times 10^{-4}$M (−1.2%) | $4.22 \times 10^{-4}$M (−20.0%) |
| (53) | $<10^{-4}$M | $1.17 \times 10^{-4}$M | $2.40 \times 10^{-4}$M |
| (55) | $1.32 \times 10^{-4}$M | $3.94 \times 10^{-4}$M | — |
| (56) | $1.14 \times 10^{-4}$M | $4.05 \times 10^{-4}$M | — |
| (57) | $<10^{-4}$M | $2.48 \times 10^{-4}$M | — |
| (58) | $8.13 \times 10^{-6}$M (3.0%) | $4.73 \times 10^{-5}$M (13.5%) | — |
| (59) | $1.23 \times 10^{-5}$M (−2.0%) | $6.84 \times 10^{-5}$M (−2.7%) | $2.79 \times 10^{-4}$M (−3.0%) |
| (60) | $<10^{-4}$M | $2.79 \times 10^{-4}$M | — |
| (61) | $<10^{-4}$M | $1.07 \times 10^{-4}$M | — |
| (62) | $4.52 \times 10^{-6}$M | $3.00 \times 10^{-5}$M | $7.50 \times 10^{-5}$M |
| (63) | $4.22 \times 10^{-5}$M | $1.12 \times 10^{-4}$M | — |
| (64) | $1.57 \times 10^{-4}$M | $2.34 \times 10^{-4}$M | $4.95 \times 10^{-4}$M |
| (65) | $<10^{-4}$M | $3.45 \times 10^{-4}$M | — |
| (67) | $4.68 \times 10^{-5}$M | $2.11 \times 10^{-4}$M | $9.44 \times 10^{-4}$M |
| (68) | $2.82 \times 10^{-6}$M | $1.95 \times 10^{-5}$M | — |
| (69) | $4.32 \times 10^{-6}$M | $4.62 \times 10^{-5}$M | — |
| (70) | $<10^{-4}$M | $1.59 \times 10^{-4}$M | — |
| (71) | $1.23 \times 10^{-5}$M | $5.43 \times 10^{-5}$M | — |
| (72) | $3.55 \times 10^{-5}$M | $6.31 \times 10^{-5}$M | $2.11 \times 10^{-4}$M |
| (73) | $<10^{-4}$M | $1.15 \times 10^{-4}$M | $2.41 \times 10^{-4}$M |
| (74) | $<10^{-4}$M | $1.08 \times 10^{-4}$M | $5.46 \times 10^{-4}$M |
| (76) | $3.89 \times 10^{-5}$M | $7.33 \times 10^{-5}$M | $3.05 \times 10^{-4}$M |
| (77) | $4.73 \times 10^{-6}$M | $5.01 \times 10^{-5}$M | — |
| (78) | $8.41 \times 10^{-6}$M (−6.2%) | $7.50 \times 10^{-5}$M (−25.0%) | — |
| (79) | $<10^{-4}$M | $1.35 \times 10^{-4}$M | $6.80 \times 10^{-4}$M |
| (81) | $3.55 \times 10^{-5}$M (−10.5%) | $5.75 \times 10^{-5}$M (−15.0%) | — |
| (82) | $<10^{-4}$M | $1.68 \times 10^{-4}$M | — |
| (83) | $1.95 \times 10^{-5}$M | $3.63 \times 10^{-4}$M | — |
| (84) | $3.59 \times 10^{-5}$M (−3.0%) | $5.75 \times 10^{-5}$M (−6.5%) | $1.26 \times 10^{-4}$M (−11.5%) |
| (85) | $1.58 \times 10^{-6}$M (−1.2%) | $9.77 \times 10^{-6}$M (−0.8%) | — |
| (86) | $3.00 \times 10^{-5}$M (1.5%) | $1.25 \times 10^{-4}$M (8.5%) | — |
| (87) | $<10^{-4}$M | $3.27 \times 10^{-4}$M | — |
| (88) | $<10^{-4}$M | $2.02 \times 10^{-4}$M | $8.56 \times 10^{-4}$M |
| (89) | $<10^{-4}$M | $6.57 \times 10^{-4}$M | — |
| (90) | $1.81 \times 10^{-4}$M | $3.45 \times 10^{-4}$M | $3.94 \times 10^{-4}$M |
| (91) | $1.33 \times 10^{-5}$M (2.3%) | $1.19 \times 10^{-4}$M (16.0%) | $7.50 \times 10^{-4}$M |
| (92) | $4.73 \times 10^{-6}$M (1.0%) | $3.76 \times 10^{-5}$M (6.0%) | — |
| (93) | $3.76 \times 10^{-4}$M | $4.65 \times 10^{-4}$M | — |
| (94) | $<10^{-4}$M | $<10^{-4}$M | $4.17 \times 10^{-4}$M |
| (95) | $1.78 \times 10^{-6}$M (2.8%) | $1.82 \times 10^{-5}$M (16.3%) | $9.44 \times 10^{-5}$M |
| (96) | $1.23 \times 10^{-4}$M | $3.74 \times 10^{-4}$M | — |
| (97) | $4.52 \times 10^{-6}$M (−1.0%) | $5.07 \times 10^{-5}$M (−3.0%) | — |
| (98) | $5.96 \times 10^{-6}$M | $3.67 \times 10^{-5}$M | — |
| (100) | $5.43 \times 10^{-6}$M (1.8%) | $1.88 \times 10^{-5}$M (3.5%) | — |
| (101) | $1.68 \times 10^{-6}$M (−1.0%) | $1.95 \times 10^{-5}$M (−2.8%) | $8.91 \times 10^{-5}$M (0.0%) |
| (102) | $2.51 \times 10^{-6}$M (−0.2%) | $4.03 \times 10^{-5}$M (−5.2%) | — |
| (103) | $3.00 \times 10^{-6}$M (−2.0%) | $3.43 \times 10^{-5}$M (0.5%) | $1.62 \times 10^{-4}$M (1.2%) |

TABLE 2-continued

| Compound | EC$_{20}$ | EC$_{50}$ | EC$_{100}$ |
|---|---|---|---|
| (104) | 1.15 × 10$^{-5}$M (−3.5%) | 5.19 × 10$^{-5}$M (−0.5%) | — |
| (105) | <10$^{-4}$M | 2.21 × 10$^{-4}$M | — |
| (106) | 1.02 × 10$^{-4}$M | 2.45 × 10$^{-4}$M | 4.47 × 10$^{-4}$M |
| (107) | 1.62 × 10$^{-5}$M (−6.6%) | 1.00 × 10$^{-4}$M (−19.5%) | — |
| (108) | 4.42 × 10$^{-5}$M | 1.26 × 10$^{-4}$M | — |
| (110) | 1.05 × 10$^{-4}$M | 1.78 × 10$^{-4}$M | — |
| (111) | 1.82 × 10$^{-5}$M (−9.8%) | 9.77 × 10$^{-5}$M (−27.0%) | — |
| (114) | 6.46 × 10$^{-6}$M (−1.8%) | 5.31 × 10$^{-5}$M (−4.0%) | 1.00 × 10$^{-3}$M (−1.3%) |
| (115) | 1.53 × 10$^{-5}$M | 8.13 × 10$^{-5}$M | 2.02 × 10$^{-4}$M |
| (116) | 1.53 × 10$^{-5}$M (−10.0%) | 6.03 × 10$^{-5}$M | — |
| (118) | 1.00 × 10$^{-5}$M (−5.0%) | 4.90 × 10$^{-5}$M (−21.2%) | — |
| (119) | 3.76 × 10$^{-5}$M | 8.41 × 10$^{-5}$M | — |
| Theophylline (Control) | 7.24 × 10$^{-5}$M (7.3%) | 3.02 × 10$^{-4}$M (20.0% | — |

As apparent from the table listed above, all of the compounds according to the present invention have the effect of enhancing heart muscle contracting force.

Also, some of the compounds enhances selectively heart muscle contracting force without the increase of heart rate. In the case of the control drug, as apparent from the results of Table 2, heart rate was increased significantly.

Test Method 2: Effect on Heart Muscle Contracting Force

The compounds according to the present invention was evaluated with reference to the effect on heart muscle contracting force by means of a method using an anesthetized dog.

Beagle dogs having a body weight of 8–11 kg were used for the experiment. They were anesthetized by intraperitoneal administration of a sodium salt of pentobarbital (35 mg/kg) and, if necessary, of additional small amount of the sodium salt of pentobarbital. Anesthesia was maintained by administering the sodium salt of pentobarbital in a dose of 5 mg/kg/hour through a cannula inserted within a vein. Breathing was performed through a cannula inserted within a trachea with a respirator. The maximum accelerations of contracting the left atrial muscle (LV-dp/dt$_{max}$) were measured with a pressure transducer inserted into the left ventricle. Compounds tested was administered in a dose of 1 mg/kg through a cannula inserted into the other vein. The parameters were expressed as the increasing rate (Δ%) after dosing of the drug with the value at the initiation when the drug was administered being set as 100%.

| Compound | ΔLV-dP/dt$_{max}$ (%) |
|---|---|
| Theophylline | 18.8 |
| (20) | 41.7 |
| (51) | 41.2 |
| (62) | 60.0 |
| (85) | 25.0 |
| (95) | 46.9 |
| (98) | 57.1 |

What is claimed is:

1. A quinolone derivative represented by the general formula or a pharmaceutically acceptable salt thereof:

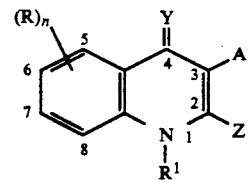

[1]

wherein respective substituents are defined as follows:
A is a hydrogen atom;
Y is an oxygen or sulfur atom;
R is a linear or branched alkoxy or alkenyloxy group having 1–4 carbon atoms, a benzyloxy group, a linear or branched alkyl or alkenyl group having 1–4 carbon atoms, a dialkylamino group having 1–4 carbon atoms, a phenyl group, a chlorine atom, a benzoyl group, an alkylsulfenyl, alkylsulfinyl or alkylsulfonyl group having 1–4 carbon atoms, or a methylenedioxy group;
n denotes 2;
R's are placed at the positions 6 and 7 or 6 and 8 and may be the same or different;
R$^1$ is a hydrogen atom, a linear or branched alkyl or alkenyl group having 1–6 carbon atoms, a benzyl or substituted benzyl group having a substituent which is a C$_1$–C$_4$ lower alkoxy group and/or a halogen atom; and
Z is a hydrogen atom, a cyclopropyl group, a 2- or 3-thienyl group, a 2- or 3-furyl group, a 2- or 3-pyrrolyl group of 2-, 3 -or 4- pyridyl group; provided that when Z and R$^1$ are both hydrogen and Y is oxygen one R may not be methoxy or chlorine if the other R is methoxy or chlorine.

2. A quinolone derivative selected from the group consisting of:

5-hydroxy-6-methoxy-4(1H)-quinolone;
6-hydroxy-5-methoxy-4(1H)-quinolone;
8-hydroxy-7-methoxy-4(1H)-quinolone;
5-benzyloxy-6-methoxy-4(1H)-quinolone;
3-ethoxycarbonyl-5-methoxy-8-methoxymethoxy-4(1H)-quinolone;
8-cyano-4(1H)-quinolone;
5-cyano-4(1H)-quinolone;
6-acetoxy-4(1H)-quinolone;
6-acetoxy-1-acetyl-4(1H)-quinolone;
8-methoxy-1-methyl-4(1H)-quinolone;
5,8-diethoxy-4(1H)-quinolone;
8-i-propyl-4(1H)-quinolone;
8-methoxy-5-methyl-4(1H)-quinolone;
5-methoxy-8-phenyl-4(1H)-quinolone;
5-methoxy-8-methylsulfenyl-4(1H)-quinolone;
6,7,8-trimethoxy-4(1H)-quinolone;
5-hydroxy-7-methoxy-4(1H)-quinolone;
8-cyano-3-ethoxycarbonyl-4(1H)-quinolone;
6,7-dimethoxy-3-methoxycarbonyl-1-methyl-4(1H)-quinolone;
3-ethoxycarbonyl-1-ethyl-6-methyl-4(1H)-quinolone;
7-ethoxy-3-ethoxycarbonyl-1-ethyl-6-methoxy-4(1H)-quinolone;
3-ethoxycarbonyl-8-methoxy-4(1H)-quinolone;
3-ethoxycarbonyl-8-methoxy-5-methyl-4(1H)-quinolone;
3-ethoxycarbonyl-8-methoxy-5-phenyl-4(1H)-quinolone;

7,8-dimethoxy-3-ethoxycarbonyl-1-ethyl-4(1H)-quinolone;
3-ethoxycarbonyl-1-ethyl-8-methoxy-6-methylsulfinyl-4(1H)-quinolone;
3-ethoxycarbonyl-1-ethyl-8-methoxy-6-methylsulfonyl-4(1H)-quinolone;
6,7-dimethoxy-3-hydroxymethyl-4(1H)-quinolone;
6,7-dimethoxy-3-hydroxymethyl-1-methyl-4(1H)-quinolone;
3-carboxyl-1-methyl-5,6,7-trimethoxy-4(1H)-quinolone;
8-acetyl-4(1H)-quinolone;
6-cyanomethyl-4(1H)-quinolone;
6-[2-trans-(2,5-dimethoxyphenyl)vinyl]-4(1H)-quinolone;
7,8-dimethyl-1-ethyl-4(1H)-quinolone;
7-[(1,3-dioxolan-2-yl)methoxy]-6-methoxy-4(1H)-quinolone;
6-methoxy-7-(2-methoxy)ethoxy-4(1H)-quinolone;
6-methoxy-7-methoxymethoxy-4(1H)-quinolone;
1-ethyl-7-methyl-4(1H)-quinolone;
1-ethyl-6-methyl-4(1H)-quinolone;
1-ethyl-5-hydroxy-8-methyl-4(1H)-quinolone;
6-(2-hydroxy)ethyl-4(1H)-quinolone;
6-ethoxycarbonyl-4(1H)-quinolone;
1-ethyl-8-methoxy-5-phenyl-4(1H)-quinolone;
7-piperazinyl-4(1H)-quinolone;
8-(2-propenyl)-4(1H)-quinolone;
8-(2-trans-butenyl)-7-hydroxy-6-methoxy-4(1H)-quinolone;
1-ethyl-6-methoxy-4(1H)-quinolone;
6-ethoxy-1-ethyl-4(1H)-quinolone;
1,6-diethyl-4(1H)-quinolone;
6-ethoxy-3-ethoxycarbonyl-8-methoxy-4(1H)-quinolone;
6-ethoxy-3-ethoxycarbonyl-1-ethyl-8-methoxy-4(1H)-quinolone;
8-ethoxy-3-ethoxycarbonyl-1-ethyl-6-methoxy-4(1H)-quinolone;
5-ethoxy-3-[(2-ethoxy)ethoxycarbonyl]-8-methoxy-4(1H)-quinolone;
3-ethoxycarbonyl-8-methoxy-4(1H)-thioquinolone;
7,8-dimethyl-3-ethoxycarbonyl-1-ethyl-4(1H)-quinolone;
5-acetoxy-3-ethoxycarbonyl-1-ethyl-8-methyl-4(1H)-quinolone;
3-ethoxycarbonyl-8-phenylsulfonyl-4(1H)-quinolone;
6-diethylamino-3-ethoxycarbonyl-8-methyl-4(1H)-quinolone;
1,6-diethyl-3-ethoxycarbonyl-4(1H)-quinolone;
3-carboxyl-6-ethoxy-1-ethyl-7-methoxy-4(1H)-quinolone;
3-carboxyl-1-ethyl-5-methyl-4(1H)-quinolone;
3-carboxyl-7,8-dimethyl-6-ethoxy-1-ethyl-4(1H)-quinolone;
3-carboxyl-6-methoxy-1,7,8-trimethyl-4(1H)-quinolone;
3-carboxyl-1-ethyl-6-methyl-4(1H)-quinolone;
3-carboxyl-8-methoxy-5-phenyl-4(1H)-quinolone;
3-carboxyl-7-ethoxy-6-methoxy-1-methyl-4(1H)-quinolone;
3-carboxyl-7-ethoxy-6-methoxy-1-n-propyl-4(1H)-quinolone;
2-cyclopropyl-4(1H)-quinolone;
1-ethyl-2-(2-thienyl)-4(1H)-quinolone;
5-benzyloxy-6-methoxy-2-(3-pyridyl)-4(1H)-quinolone;
6,7-dimethoxy-3-(4-phenylpiperidinyl)carbonyl-4(1H)-quinolone;
8-methoxy-5-methyl-3-(4-phenylpiperidinyl)carbonyl-4(1H)-quinolone;
8-methoxy-1-methyl-3-{1-[4-(3,4-methylenedioxybenzyl)-piperazinyl]carbonyl}-4(1H)-quinolone;
1-ethyl-3-{1-[4-(2-methoxyphenyl)piperazinyl]carbonyl}-6-methyl-4(1H)-quinolone;
3-{1-[4-(2-methoxyphenyl) piperazinyl]carbonyl}-6-methyl-4(1H)-quinolone.
6,7-dimethoxy-1-ethyl-3-{1-[4-(4-nitrophenyl)-piperazinyl]carbonyl}-4(1H)-quinolone;
6-[2-trans-(2,5-dimethoxyphenyl)vinyl]-1-ethyl-4(1H)-quinolone; and
2-cyclopropyl-1-ethyl-4(1H)-quinolone.

3. A pharmaceutical composition comprising an effective amount of a compound according to claim 1 and an acceptable carrier.

4. A pharmaceutical composition comprising an effective amount of a compound according to claim 2 and an acceptable carrier.

* * * * *